(12) United States Patent
Andjelic et al.

(10) Patent No.: US 8,455,418 B2
(45) Date of Patent: *Jun. 4, 2013

(54) POLYGLYCERYL COMPOUNDS COMPRISING A METHYL GLUCOSIDE OR SORBITAN REMNANT AND COMPOSITIONS CONTAINING SAME

(75) Inventors: Sasa Andjelic, Nanuet, NY (US); Modesto Erneta, Princeton Junction, NJ (US); Michael J. Fevola, Belle Mead, NJ (US); Frank C. Sun, Branchburg, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 49 days.

This patent is subject to a terminal disclaimer.

(21) Appl. No.: 13/075,346

(22) Filed: Mar. 30, 2011

(65) Prior Publication Data
US 2012/0122758 A1 May 17, 2012

Related U.S. Application Data

(60) Provisional application No. 61/413,712, filed on Nov. 15, 2010.

(51) Int. Cl.
*C11D 3/20* (2006.01)
*C11D 3/37* (2006.01)

(52) U.S. Cl.
USPC ........... 510/130; 510/119; 510/421; 510/470; 510/505

(58) Field of Classification Search
USPC .................. 510/119, 130, 421, 470, 505
See application file for complete search history.

(56) References Cited

U.S. PATENT DOCUMENTS

| | | | |
|---|---|---|---|
| 6,991,799 B2 | 1/2006 | Pham et al. | |
| 2003/0202948 A1* | 10/2003 | Koini et al. | 424/59 |
| 2010/0184871 A1* | 7/2010 | Bevinakatti et al. | 514/785 |
| 2010/0202984 A1* | 8/2010 | Langhals et al. | 424/59 |
| 2012/0121524 A1* | 5/2012 | Muller et al. | 424/60 |

FOREIGN PATENT DOCUMENTS

| | | |
|---|---|---|
| JP | 2006348073 A | 12/2006 |
| WO | WO 2008/142374 | 11/2008 |
| WO | WO 2009/016375 | 2/2009 |

OTHER PUBLICATIONS

G. Rokicki et al., "Hyperbranched aliphatic polyethers obtained from environmentally benign monomer: glycerol carbonate", *Green Chem.* 2005, 7, 529-539.

Rakoczy, et al., "Hyperbranched polyethers obtained from glycerol carbonate", Warsaw University of Tecnology, Faculty of Chemistry, ul. Noakowskiego 3, 00-664, Warsaw, Poland, pp. 1-6, 2005.

* cited by examiner

*Primary Examiner* — Charles Boyer

(57) ABSTRACT

Provided are compositions comprising one or more compounds having a structure comprising a node structure with from four to twelve carbon atoms, one or more (poly)glyceryl groups, and one or more hydrophobic moieties, wherein each of the one or more (poly)glyceryl groups is linked to the node structure by a first primary linking group, the one or more hydrophobic moieties are each independently linked either to the node structure by a primary linking group or to one of the (poly)glyceryl groups by a secondary linking group, and wherein the polyglyceryl thickener has an average degree of glyceryl polymerization of from greater than 3 to less than about 11 and an average number of hydrophobic groups per primary linking group of about 0.35 or greater. Also provided are polyglyceryl compounds, compositions comprising water, a surfactant, and a polyglyceryl thickener, as well as, methods of making polyglyceryl compounds and compositions of the present invention.

26 Claims, 4 Drawing Sheets

POLYGLYCERYL COMPOUNDS COMPRISING A METHYL GLUCOSIDE OR SORBITAN REMNANT AND COMPOSITIONS CONTAINING SAME

CROSS-REFERENCE TO RELATED APPLICATION

This application claims the benefit of priority of the provisional application, Application Ser. No. 61/413,712, filed Nov. 15, 2010 and incorporated herein in its entirety by reference.

FIELD OF INVENTION

The present invention relates to polyglyceryl thickeners and compositions comprising polyglyceryl thickeners that are useful in a variety of applications including cleansing of the human body.

DESCRIPTION OF THE RELATED ART

Synthetic detergents, such as cationic, anionic, amphoteric, and non-ionic surfactants, are used widely in a variety of detergent and cleansing compositions to impart cleansing properties thereto. In addition, in certain compositions (e.g. personal care compositions such as shampoos, washes, etc.), it may be desirable to combine surfactants and ingredients such as thickeners to achieve relatively a desirable balance of properties such as mildness, foam volume, foam stability, and rheological behavior.

A commonly used class of thickeners are amphiphilic molecules that have large hydrophilic head groups and are highly ethoxylated, often comprising greater than 100 moles of ethylene oxide (EO). Unfortunately, ethoxylation requires tremendous volumes of EO, a gaseous petrochemical derivative synthesized via air-oxidation of ethylene gas. In addition to being a difficult-to-handle chemical with significant health and safety risks, EO is considered by many to be unsustainable in the long term due to finite reserves of crude oil and natural gas in the world. Furthermore, a byproduct of ethoxylation processes is the cyclic ether 1,4-dioxane, a suspected carcinogen at high exposure levels. Ethoxylated materials typically contain trace levels (10-100 ppm) of 1,4-dioxane, and special separation processes (e.g. vacuum stripping) must be employed to reduce the level of 1,4-dioxane to undetectable levels. When present in cleansing compositions at trace levels, 1,4-dioxane is not considered to be a credible health or safety risk. Nevertheless, negative publicity associated with 1,4-dioxane has provided motivation to seek products that do not have ethoxylated materials.

The inventors have recognized that it would be desirable to replace synthetic ethoxylated thickeners with more natural and renewable materials. However, natural thickeners such as vegetable gums typically have a stringy, pseudoplastic, and/or elastic rheology that is less aesthetically desirable. Accordingly, the inventors have recognized that it is highly desirable to formulate compositions that have more naturally-derived and/or renewable thickeners to alleviate the aforementioned drawbacks. The inventors have further recognized that thickeners that do not require ethoxylation are highly desirable, particularly thickeners that are capable of thickening a range of personal care product formulations in manner that is aesthetically acceptable to consumers.

SUMMARY OF THE INVENTION

The present invention provides polyglyceryl thickeners that overcome the disadvantages of the prior art and are capable of enhancing the viscosity of compositions to which they are added.

According to one aspect, the present invention provides polyglyceryl compositions comprising one or more compounds, having a structure comprising a node structure with from four to twelve carbon atoms, one or more (poly)glyceryl groups, and one or more hydrophobic moieties, wherein each of the one or more (poly)glyceryl groups is linked to the node structure by a first primary linking group, the one or more hydrophobic moieties are each independently linked either to the node structure by a primary linking group or to one of the (poly)glyceryl groups by a secondary linking group, and wherein the polyglyceryl thickener has an average degree of glyceryl polymerization of from greater than 3 to about 11 and an average number of hydrophobic groups per primary linking group of about 0.35 or greater.

According to another aspect, the present invention provides polyglyceryl compounds, and/or compositions comprising one or more compounds, of the Formula I:

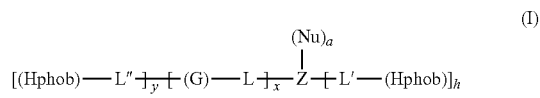

wherein:
Z is a node structure comprising from four to twelve carbon atoms;
each G is an independently selected (poly)glyceryl group;
each (Hphob) is an independently selected hydrophobic moiety;
each L is an independently selected primary linking group;
each L' is an independently selected primary linking group;
each L" is an independently selected secondary linking group;
each (Nu) is an independently selected nucleophilic group;
x is from 1 to 12;
h is from 0 to 11;
y is from 0 to 5;
a is from 0 to 11;
the sum of x+h+a is from 4 to 12; and
the sum of h+y is from 1 to 12.

According to another aspect, the present invention provides compositions comprising a base comprising water and a surfactant, and a polyglyceryl thickener having a structure comprising a node structure with from four to twelve carbon atoms, one or more (poly)glyceryl groups, and one or more hydrophobic moieties, wherein each of the one or more (poly)glyceryl groups is linked to the node structure by a first primary linking group, the one or more hydrophobic moieties are each independently linked either to the node structure by a primary linking group or to one of the (poly)glyceryl groups by a secondary linking group, and wherein the polyglyceryl thickener has an average degree of glyceryl polymerization of greater than 3 and an average number of hydrophobic groups per primary linking group of about 0.35 or greater, and wherein said polyglyceryl thickener is present in a concentration sufficient to increase the Zero Shear Viscosity of the base by about 100 cP or more.

According to other aspects, the present invention provides methods of making polyglyceryl thickeners, and methods of cleansing the human body by contacting the body with a composition of the present invention.

DESCRIPTION OF PREFERRED EMBODIMENTS

Figure 1:
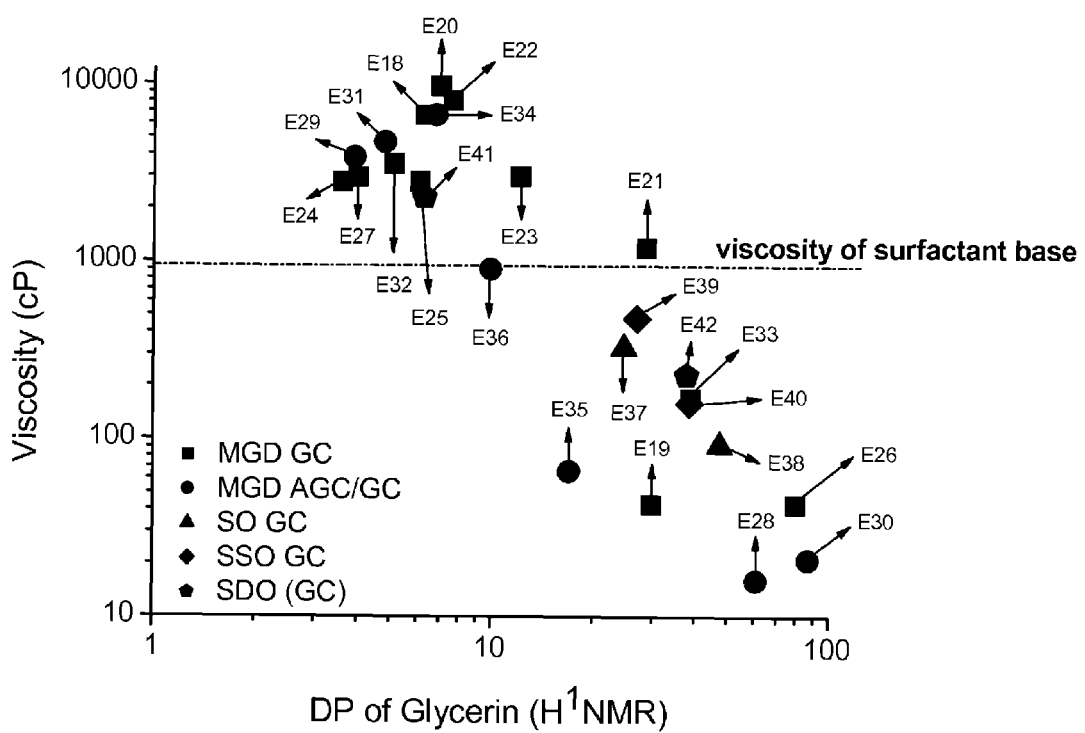
FIG. 1 is a graphical depiction of the relative viscosity compared to base as function of $DP_g$ measured for certain compositions of the claimed invention.

All percentages listed in this specification are percentages by weight, unless otherwise specifically mentioned.

As used herein, the term "healthcare" refers to the fields of personal care and medical care including, but not limited to, infant care, oral care, sanitary protection, skin care, including the treatment of adult or infant skin to maintain the health of the skin, improve the health of the skin, and/or improve the appearance of the skin, wound care, including the treatment of a wound to assist in the closure or healing of a wound, and/or to reduce the pain or scarring associated with the wound, women's health, including the treatment of tissue in the internal or external vaginal area and/or breast, maintaining or improving the health of such tissue or skin, repairing such tissue or skin, reducing irritation of such tissue or skin, maintaining or improving the appearance of such tissue or skin, and improving or enhancing sexual function associated with such tissue or skin, and the like.

As noted above, applicants have discovered unexpectedly that certain polyglyceryl compounds or compositions can be used to thicken cosmetic and personal care bases. In particular, applicants have noted the unexpected properties associated with the use of certain embodiments of polyglyceryl compositions that have both an average degree of glyceryl polymerization greater than three and at least about 0.35 average hydrophobic moieties per primary linking group. The resulting compositions may be suitable for use as cleansing and/or rinse-off compositions.

In certain embodiments, polyglyceryl compounds and compositions of the present invention may be described with reference to the following structure (Formula I):

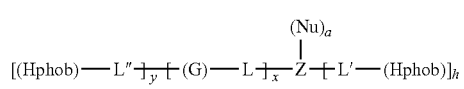
(I)

where, according to this embodiment:
Z is a node structure;
each G is an independently selected (poly)glyceryl group;
each L is an independently selected primary linking group (linking a (poly)glyceryl group to the node structure);
x is the number of (poly)glyceryl groups per polyglyceryl molecule, which is from 1 to 12;
each (Hphob) is an independently selected hydrophobic moiety;

each L' is an independently selected primary linking group (linking a hydrophobic moiety to the node structure);
h is the number of hydrophobic moieties that are linked to the node structure via a linking group L', which is from 0 to 11;
each L" is an independently selected secondary linking group (linking a hydrophobic moiety to a glyceryl group);
y is the number of hydrophobic moieties that are linked to a (poly)glyceryl group via a secondary linking group L", which is from 0 to 5;
each (Nu) is an independently selected nucleophilic group;
a is the number of nucleophilic groups, which is from 0 to 11;
the sum of x+h+a is from 4 to 12; and
the sum of h+y is from 1 to 12.

Accordingly, polyglyceryl materials of the present invention comprise compounds having a node structure (Z) to which (poly)glyceryl units are linked via a primary linking group (L). Suitable node structures include linear, branched, or cyclic, saturated or unsaturated polynucleophile remnants comprising from four to twelve carbon atoms, and optionally, one or more heteroatoms such as oxygen, nitrogen, or sulfur. As used herein the term "polynucleophile" means a compound having a plurality of nucleophilic functional groups or groups capable of being rendered nucleophilic, for example, hydroxyl (—OH), thio (—SH), amino (—$NR_2$, where R is H or $CH_3$), carboxy (—COO—) groups, and the like. Examples of polynucleophiles include: polyols such as monosaccharides, e.g. glucose, fructose, galactose, mannose, glucosamine; $C_1$-$C_4$ glucosides, disaccharides (e.g. sucrose), sugar alcohols (e.g. sorbitol, xylitol, mannitol), anhydro sugar alcohols (e.g. sorbitan), pentaerythritol, oligoglycerols (e.g. diglycerol, triglycerol), N,N,N',N'-tetrakis(2-hydroxyethyl)ethylenediamine, N,N,N',N'-tetrakis(2-hydroxypropyl)ethylenediamine, and the like.

The term "polynucleophile remnant" as used herein refers to the structure of a polynucleophile compound with all of the terminal nucleophilic groups (e.g. hydroxyl groups) removed. For example, a polynucleophilic remnant derived from methyl glucoside would be the structure of methyl glucoside with the four hydroxyl groups removed therefrom as shown below:

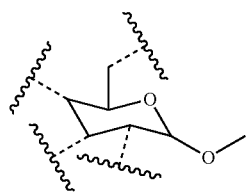

which results in a node structure which is a 5-carbon cyclic ether having a methylene at the 5-position and a methyl ether at the 1-position. Other examples include polynucleophilic remnants derived from sorbitan (wherein removal of the four hydroxyl groups results in a node structure that is a 4-carbon cyclic ether with an ethyl group at the 2-position):

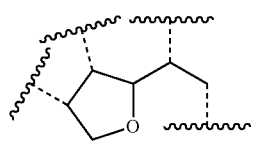

and triglycerol (wherein removal of the five hydroxyl groups results in a 1,3,-dipropoxypropane node structure):

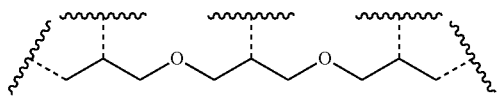

and the like. According to certain preferred embodiments, the node structure has from about 6 to about 9 carbons, in certain more preferred embodiments from about 6 to about 7 carbons. According to certain preferred embodiments, the node structure is a polynucleophile remnant derived from a polynucleophile selected from the group consisting of polyols such as monosaccharides, e.g. glucose, fructose, galactose, mannose, glucosamine; $C_1$-$C_4$ glucosides, disaccharides (e.g. sucrose), sugar alcohols (e.g. sorbitol, xylitol, mannitol), anhydro sugar alcohols (e.g. sorbitan), pentaerythritol, oligoglycerols (e.g. diglycerol, triglycerol), N,N,N',N'-tetrakis(2-hydroxyethyl)ethylenediamine, and N,N,N',N'-tetrakis(2-hydroxypropyl)ethylenediamine. In certain more preferred embodiments, the node structure is a polynucleophile remnant derived from methyl glucoside, sorbitan, diglycerol, or triglycerol, or in other more preferred embodiments, from methyl glucoside, diglycerol, or triglycerol.

The polyglyceryl materials of the present invention comprise one or more (poly)glyceryl groups (G). As used herein a "(poly)glyceryl group" means a group linked to the node through a primary linking group (L) comprising one glyceryl unit, a plurality of glyceryl units linked together in sequence, and/or one or more glyceryl units linked with co-repeat units as part of a glyceryl copolymer group. The term "glyceryl unit" means a linear, branched, and/or cyclic ether-comprising moiety that is a structural derivative of glycerol ($C_3H_8O_3$), such as units corresponding to dehydrated glycerol ($C_3H_6O_2$). Those skilled in the art will recognize, the glyceryl units may be present as single units in a particular glyceryl group or may repeat such that a plurality of such units are present in a given (poly)glyceryl group.

Examples of certain glyceryl units are represented as linear-1,4 ($L_{1,4}$) units:

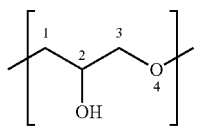

linear-1,3 ($L_{1,3}$) glyceryl units,

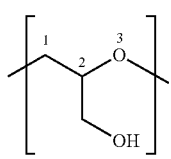

dendritic (D) glyceryl repeat units, which lead to branched and cyclic units,

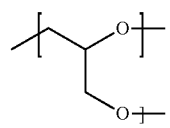

terminal-1,2 ($T_{1,2}$) units

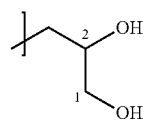

and terminal-1,3 ($T_{1,3}$) units

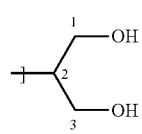

In one embodiment, the polyglyceryl thickener comprises glyceryl groups that are glyceryl copolymer groups. By "glyceryl copolymer group" it is meant that in addition to glyceryl units described above, the glyceryl group includes one or more repeat units such as oxypropylene units:

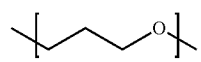

Generically:

where R=$C_1$-$C_4$ linear or branched alkyl, such as —$CH_2CH_2$—, —$CH(CH_3)CH_2$—, and —$CH_2CH_2CH_2$—, that originate from reacting optional co-monomers (such as ethylene carbonate, 1,2-propylene carbonate, and 1,3-propylene carbonate) in the formation of the polyglyceryl thickeners. Furthermore, one or more of the glyceryl groups may include $C_2$-$C_4$ acyl glyceryl units such as acetyl glyceryl units:

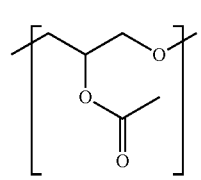 and 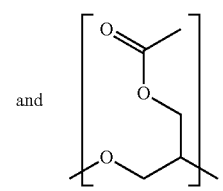

and $C_1$-$C_4$ alkyl glyceryl units, such as methyl glyceryl ether units:

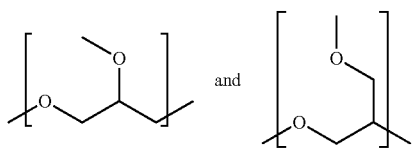

According to certain preferred embodiments, the polyglyceryl compositions of the present invention have an average degree of glyceryl polymerization ($DP_g$) greater than 3. Those skilled in the art will recognize that "average degree of glyceryl polymerization" means the number of glyceryl units per mole of polyglyceryl thickener on a number average basis. In certain preferred embodiments, the average degree of glyceryl polymerization is from about 4 to about 100 glyceryl repeat units, preferably from about 4 to about 50 glyceryl repeat units, more preferably from about 4 to about 25 glyceryl repeat units, even more preferably from about 4 to about 15 glyceryl repeat units. In certain other preferred embodiments, the average degree of glyceryl polymerization is greater than 3 to about 11. The $DP_g$ of a polyglyceryl composition is calculated in accord with the present invention using nuclear magnetic resonance (NMR) techniques in accord with the Average Degree of Glyceryl Polymerization Measurement Procedure described herein below.

As discussed above, each of the one or more of the (poly) glyceryl groups are linked to the node structure by a primary linking group (L). By "linked to the node structure by a primary linking group," it is meant that the (poly)glyceryl group is directly linked to the node structure with only a primary linking (functional) group therebetween. The primary linking group may be, for example, the functional moieties that when linked to at least two carbon atoms form ethers, esters, carbamates (urethanes), amines, amides, ketones, carbonates, thioethers, thioesters, dithioesters, xanthates. That is, as will be understood by one of skill in the art, each primary linking group may be selected from: —O—, —C(O)O—, —N(H)C(O)O—, —N(R)$_2$—, —N(R)C(O)—, —C(O)—, —OC(O)O—, —S—, —C(S)O—, —C(S)S—, —OC(S)S—, where each R is independently H or methyl. According to certain preferred embodiments, the primary linking group is —O—, amine, or carbamate.

In certain embodiments, the primary linking group is derived from the nucleophilic groups of the polynucleophile that was used in the process of making the polyglyceryl thickener. For example, if a polynucleophile bearing hydroxyl groups is reacted with glycerol carbonate then the resulting node structure will be substituted with (poly)glyceryl groups covalently linked to the node by primary linking groups that are ether bonds (i.e. the linking group is —O—). As one skilled in the art would readily understand, in embodiments in which the number of glyceryl units is larger than the number of (poly)glyceryl groups, certain glyceryl units present in the polyglyceryl thickener, rather than bonded to the node structure, are, for example, bonded to neighboring glyceryl units.

The polyglyceryl materials further include one or more terminal hydrophobic moieties (Hphob). By "hydrophobic moieties," is it meant nonpolar moieties that contains at least one of the following: (a) a carbon-carbon chain of at least six carbons in which none of the six carbons is a carbonyl carbon or has a hydrophilic moiety bonded directly to it; (b) three or more alkyl siloxy groups (—[Si(R)$_2$—O]—); and/or (c) three or more oxypropylene groups in sequence. A hydrophobic moiety may be, or include, linear, cyclic, aromatic, saturated or unsaturated groups. Preferred hydrophobic moieties include 9 or more carbon atoms, more preferably from 11 to 30 carbon atoms, even more preferably from 15 to 26 carbon atoms, and most preferably from 17 to 24 carbon atoms.

Other examples of hydrophobic moieties include groups such as poly(oxypropylene), poly(oxybutylene), poly(dimethylsiloxane), and fluorinated hydrocarbon groups containing a carbon chain of at least six carbons in which none of the six carbons has a hydrophilic moiety bonded directly to it, and the like.

Some specific examples of hydrophobic moieties include linear or branched, saturated or unsaturated alkyl moieties, e.g. linear or branched, saturated or unsaturated $C_{10}$-$C_{30}$ alkyl, such as decyl, undecyl, dodecyl (lauryl), tridecyl, tetradecyl (myristyl), pentadecyl, hexadecyl (cetyl, palmityl), heptadecyl, heptadecenyl, hepta-8-decenyl, hepta-8,11-decenyl, octadecyl (stearyl), nonadecyl, eicosanyl, henicosen-12-yl, henicosanyl, docosanyl (behenyl), and the like. Certain preferred hydrophobic moieties include heptadecyl, heptadecenyl, hepta-8-decenyl, hepta-8,11-decenyl and the like.

Each terminal hydrophobic moiety of a polyglyceryl material of the present invention may be bound either to the node structure by a primary linking functional group (L') or to a (poly)glyceryl group by a secondary linking group (L"). Any suitable and preferred moiety as described above for primary linking group (L) may also be suitable and/or preferred as a primary linking group (L') or secondary linking group (L").

In certain embodiments, the primary linking group is derived from the nucleophilic groups of the polynucleophile that were consumed in the process of bonding the hydrophobic moiety to the polynucleophile. For example, if a polynucleophile bearing hydroxyl groups (i.e. a polyol) is reacted with fatty acids under condensation reaction conditions, then the resulting node structure will be substituted with hydrophobic moieties covalently linked to the node structure by primary linking groups that are ester functional groups (—C(O)—). Alternatively, the primary linking functional group may be derived from a difunctional reagent used to covalently bind the hydrophobic moiety to the polynucleophilic node. For example, if a polynucleophile bearing hydroxyl groups (i.e. a polyol) is reacted with a diisocyanate, followed by reaction with a fatty alcohol, then the resulting node structure will be substituted with hydrophobic moieties covalently linked to the node structure by primary linking groups that are carbamate (urethane) functional groups.

Preferably, polyglyceryl materials of the present invention are sufficiently substituted with hydrophobic moieties such that the polyglyceryl compositions have an average number of hydrophobic moieties per primary linking group of about 0.35 or greater. By average hydrophobic moieties per primary linking group, it is meant the quotient of the average number of hydrophobic moieties divided by (the sum of average number of primary linking groups (L) and (L')) present in the polyglyceryl composition. In certain embodiments, the polyglyceryl composition has from about 0.35 average hydrophobic moieties per primary linking group, to about 0.55 average hydrophobic moieties per primary linking group. Those of skill in the art will recognize that certain polynucleophiles and/or starting materials of the formula Node-(L'-Hphob)$_h$ may be commercially available as a mixture of mono-, di-, and/or tri-hydrophobically-substituted species. Thus the average number of hydrophobic moieties per linking group may be represented by a non-integer average value. For the purposes of clarity, the following example calculation is provided: for example, for a nominal sorbitan dioleate ester comprising 75 mol % disubstituted sorbitan and 25 mol % monosubstituted sorbitan, the average degree hydrophobic substitution (i.e. average degree of esterification) would be equal to 2(0.75)+1(0.25)=1.75 hydrophobic moieties per molecule. Since the sorbitan node bears four possible primary linking groups, the average number of hydrophobic moieties per primary linking group is equal to 1.75/4=0.44.

In certain embodiments, on average, the polyglyceryl material is sufficiently substituted with hydrophobic moieties such that the polyglyceryl material has about 1.5 or more hydrophobic moieties per molecule, preferably from about 1.5 to about 2.2 hydrophobic moieties per molecule. For example, in the example calculation above the polyglyceryl sorbitan dioleate would have 1.75 hydrophobic moieties per molecule.

While a variety of structures have been described for polyglyceryl thickeners of the present invention have been described, examples of particularly suitable polyglyceryl thickeners include those comprising compounds of the formulae:

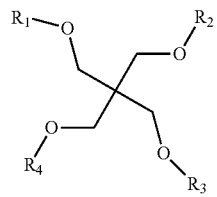

wherein $R_1$-$R_4$ are each independently either -L'-Hphob or -L-(G), provided that the thickener has on average about 1.5 or more -L'-Hphob per molecule. Such compounds are preferably derived from pentaerythritol.

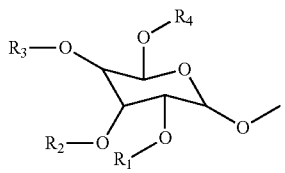

wherein $R_1$-$R_4$ are each independently either -L'-Hphob or -L-(G), provided that the thickener has on average about 1.5 or more -L'-Hphob per molecule. Such compounds are preferably derived from methyl glucose.

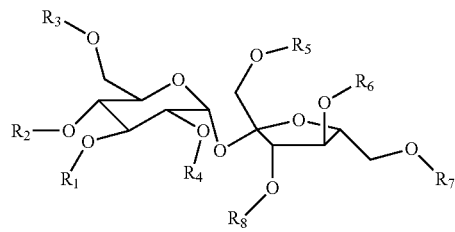

wherein $R_1$-$R_8$ are each independently either -L'-Hphob or -L-(G), provided that the thickener has on average about 1.5 or more -L'-Hphob per molecule. Such compounds are preferably derived from sucrose.

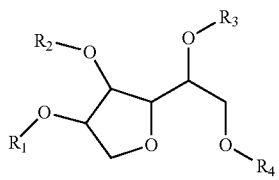

wherein $R_1$-$R_4$ are each independently either -L'-Hphob or -L-(G), provided that the thickener has on average about 1.5 or more -L'-Hphob per molecule. Such compounds are preferably derived from sorbitan.

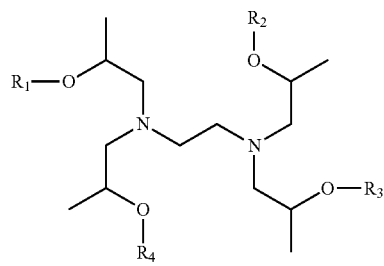

wherein $R_1$-$R_4$ are each independently either -L'-Hphob or -L-(G), provided that the thickener has on average about 1.5 or more -L'-Hphob per molecule. Such compounds are preferably derived from N,N,N',N'-tetrakis(2-hydroxypropyl) ethylenediamine.

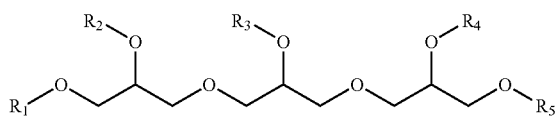

wherein $R_1$-$R_5$ are each independently either -L'-Hphob or -L-(G), provided that the thickener has on average about 1.5 or more -L'-Hphob per molecule. Such compounds are preferably derived from triglycerol.

According to certain preferred embodiments, polyglyceryl materials of the present invention derived from methyl glucose comprise polyglyceryl methyl glucose dioleate, the idealized structure for which is shown below:

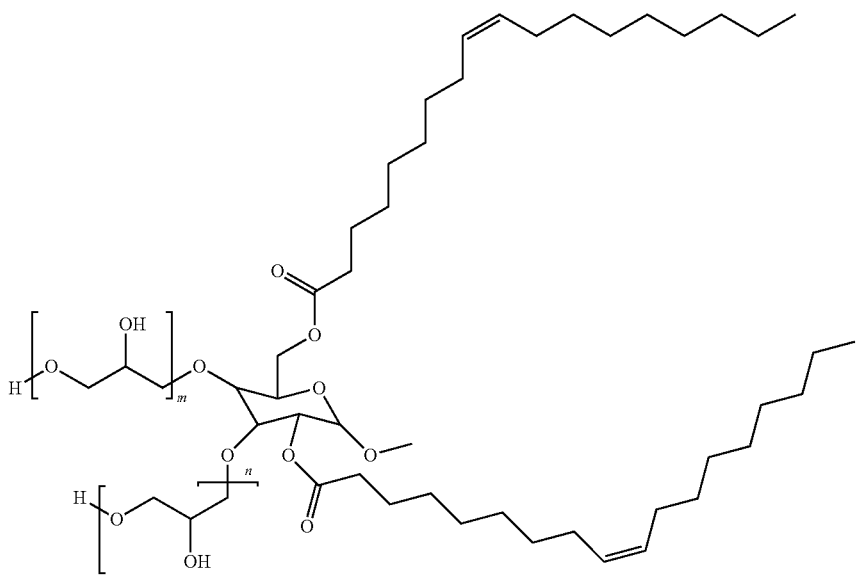

wherein, with reference to formula I,
(a) x=2, as there are two (poly)glyceryl groups [G]:

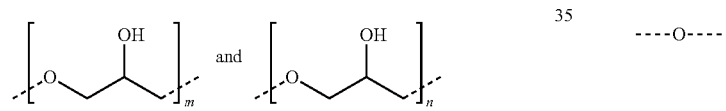

(b) h=2, as there are two hydrophobic moieties [Hphob], both of which are $C_{17}$ hydrophobes, specifically 8-heptadecenyl:

(c) the node (Z) structure is a methyl glucose remnant:

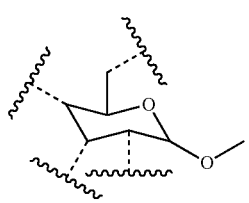

(d) residual nucleophilic groups [Nu] are absent, thus a=0
(e) each primary linking group L is an ether linkage:

----O----

(f) each primary linking group L' is an ester linkage:

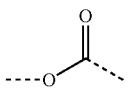

(g) Hphob-L" is absent, as such y=0. In preferred embodiments, m+n is greater than 3, preferably from about 4 to about 100, preferably from about 4 to about 50, more preferably from about 4 to about 25, even more preferably from about 4 to about 15, and even more preferably greater than 3 to about 11.

According to certain preferred embodiments, polyglyceryl materials of the present invention derived from sorbitan comprise polyglyceryl sorbitan dioleate, the idealized structure for which is shown below

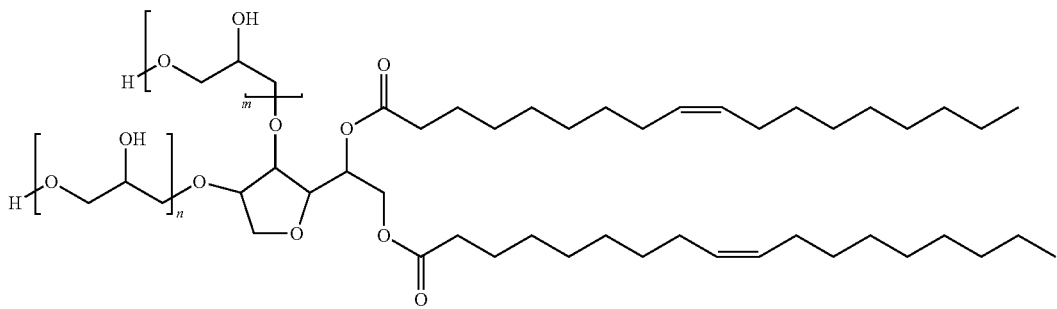

wherein, with reference to formula I,
(a) x=2, as there are two (poly)glyceryl groups [G]:

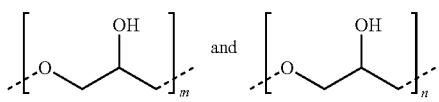 

(b) h=2, as there are two hydrophobic moieties [Hphob], both of which are $C_{17}$ hydrophobes, specifically 8-heptadecenyl:

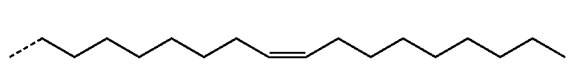

(c) the node structure is a 2-ethyltetrahydrofuranyl:

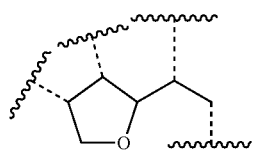

(d) residual nucleophilic groups [Nu] are absent, thus a=0
(e) each primary linking group L is an ether linkage:

----O----

(f) each primary linking group L' is an ester linkage:

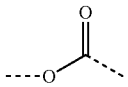

(g) Hphob-L" is absent, as such y=0. In preferred embodiments, m+n is greater than 3, preferably from about 4 to about 100, preferably from about 4 to about 50, more preferably from about 4 to about 25, even more preferably from about 4 to about 1, and even more preferably greater than 3 to about 11.

According to certain preferred embodiments, polyglyceryl materials of the present invention derived from triglycerol comprise polyglyceryl triglycerol dioleate, the idealized structure for which is shown below:

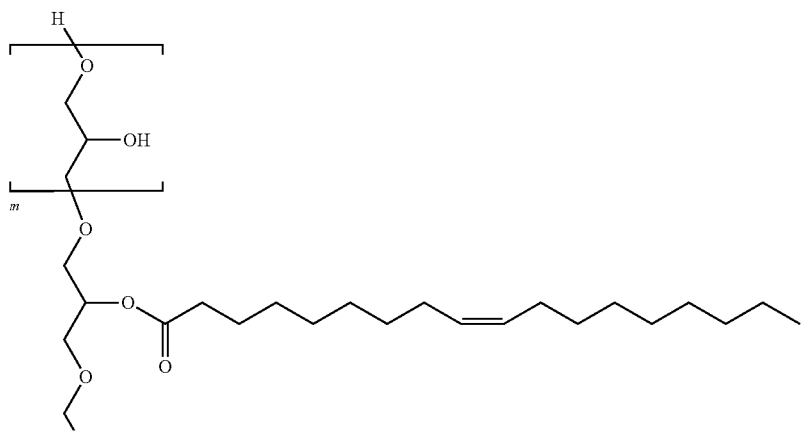

-continued

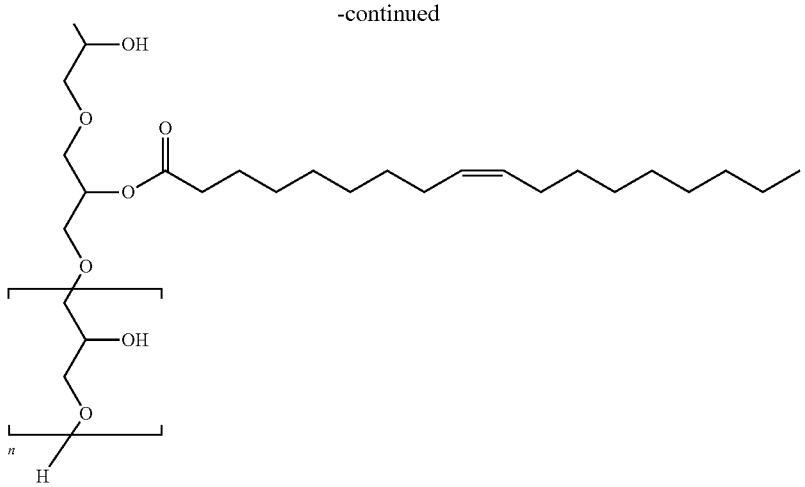

wherein, with reference to formula I, (a) x=2, as there are two (poly)glyceryl groups [G]:

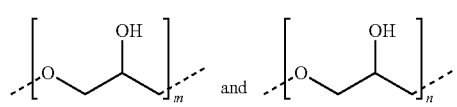

(b) h=2, as there are two hydrophobic moieties [Hphob], both of which are $C_{17}$ hydrophobes, specifically 8-heptadecenyl:

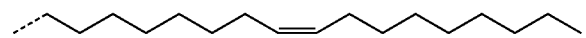

(c) the node structure is a bis(n-propyl)-1,3-propanediol ether:

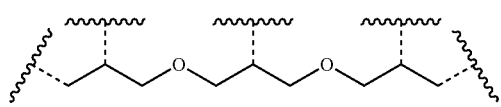

(d) there is one residual nucleophilic [Nu] (hydroxyl) group, thus a=1

(e) each primary linking group L is an ether linkage:

(f) each primary linking group L' is an ester linkage:

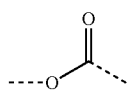

(g) Hphob-L" is absent, as such y=0. In preferred embodiments, m+n is greater than 3, preferably from about 4 to about 100, preferably from about 4 to about 50, more preferably from about 4 to about 25, even more preferably from about 4 to about 1, and even more preferably greater than 3 to about 11.

According to certain preferred embodiments, the polyglyceryl thickener compositions of the present invention comprise at least 50 mol % of polyglyceryl compounds having two hydrophobic groups, (e.g. with reference to Formula I, wherein h=2). In certain preferred embodiments, the polyglyceryl thickeners of the present invention comprise about 50 mol % to about 100 mol % of polyglyceryl compounds having two hydrophobic groups, more preferably from about 60 mol % to about 100 mol %, more preferably from about 70 mol % to about 100 mol %, more preferably from about 80 mol % to about 100 mol % of polyglyceryl compounds having two hydrophobic groups.

In certain particularly preferred embodiments, the polyglyceryl thickeners of the present invention comprise at least 50 mol %, more preferably about 50 mol % to 100%, more preferably from about 70 mol % to about 100 mol %, more preferably from about 80 mol % to about 100 mol % of polyglyceryl polyol dioleate (e.g. polyglyceryl methyl glucose dioleate, polyglyceryl sorbitan dioleate, and the like).

According to certain embodiments, for compounds of Formula I wherein Z is a polynucleophile remnant derived from sorbitan, then either: (a) x=2, h=2, a=0, y=0, and the compound has a degree of glyceryl polymerization of from greater than 3 to about 11, or (b) x is from 1 to 3, h=1, a is from 0 to 2, y is from 1 to 3, and x+h+a+y=4.

Methods of Making Polyglyceryl Thickeners

Various synthetic routes are suitable for making polyglyceryl thickeners of the present invention. In one embodiment, the polyglyceryl thickener is prepared via the base-catalyzed ring-opening addition polymerization of the monomers and optional comonomers. The (co)polymerization may be performed, for example, by first providing a polymerization initiator, e.g., a polynucleophile that has been partially substituted with hydrophobic moieties. The polymerization initiator may be represented by the following structure:

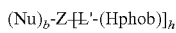

where:

Z=node structure;

Each Nu is a nucleophilic group (preferably a hydroxyl group);

Hphob=hydrophobic moiety;

Each L' is a primary linking group;

h=hydrophobic moieties per nucleophilic group (hydrophobic substitution)

b is the number of nucleophilic groups free for bonding with (poly)glyceryl groups.

Examples of suitable polymerization initiators include:

(i) glucoside diesters shown below, wherein R' is a $C_1$-$C_4$ alkyl:

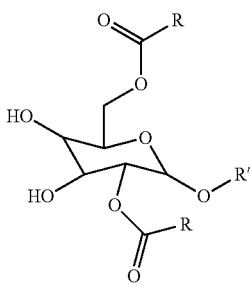

such as methyl glucose dioleate, in which R=$C_{17}$ (—RCO=oleoyl) and R'=$CH_3$.

(ii) sorbitan diesters:

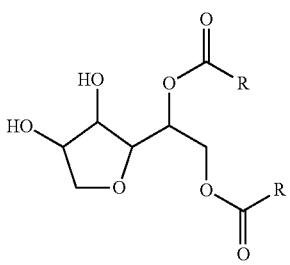

such as sorbitan dioleate, in which R=$C_{17}$ (—RCO=oleoyl);

(iii) diglyceryl diesters:

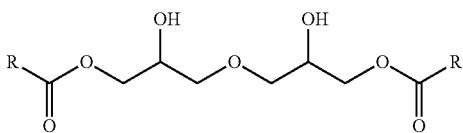

such as diglycerol dioleate, in which R=$C_{17}$ (—RCO=oleoyl); and (iv) triglyceryl diesters:

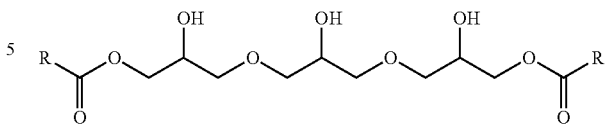

such as triglycerol dioleate, in which R=$C_{17}$ (—RCO=oleoyl).

In certain embodiments, the polymerization initiator is a compound of the above formula wherein Z is not a polynucleophile remnant derived from sorbitan. In certain preferred embodiments, the polymerization initiator may be selected from the group consisting of glucoside diesters, diglyceryl diesters, triglyceryl diesters, and combinations of two or more thereof.

To prepare polyglyceryl thickeners of the present invention, various synthetic routes may be employed, including but not limited to condensation polymerization of glyceryl monomers such as glycerol; ring-opening polymerization of such glyceryl monomers as glycerol carbonate or glycidol. Glyceryl monomers suitable for ring-opening polymerization include primary monomers, (to yield glycerol repeat units) such as glyceryl carbonate (GC), glycidol, as well as substituted monomers such as glycerol carbonate $C_1$-$C_4$ monoester (preferred is acetyl glycerol carbonate (AcGC)) and glycidol $C_1$-$C_4$ monoester. Furthermore, optional comonomers such as ethylene carbonate, 1,2-propylene carbonate, and 1,3-propylene carbonate may be used to yield a copolyether. Furthermore, glyceryl copolymers may also be derived via the ring-opening polymerization of glycerol carbonate with other cyclic carbonate monomers, such as acetylated glycerol carbonate (AcGC) to produce acetyl glyceryl units.

Typically, the molar ratio of initiator to monomer used in the synthesis is generally at least 1:3, more usually from 1:4 to 1:100, typically 1:4 to 1:75, though more usually from 1:4 to 1:50, desirably 1:4 to 1:40 and particularly from 1:5 to 1:30. Although the synthetic reaction appears robust enough to make products with average $DP_g$ greater than about 30, reaction rates may fall off somewhat at higher $DP_g$ values, which may be compensated for by top up (or continuous) addition of glycerol carbonate and/or catalyst.

To accelerate the reaction, in certain embodiments it is desirable to use a catalyst, particularly a base catalyst. Accordingly, in one embodiment, the method of making the polyglyceryl thickener includes reacting the initiator with glyceryl monomers and optional comonomers in the presence of a base catalyst. Suitable catalysts include alkali metal, particularly sodium or potassium, bases, e.g. hydroxides, particularly NaOH or KOH, carbonates, particularly $K_2CO_3$ or $Na_2CO_3$, bicarbonates, particularly $KHCO_3$ or $NaHCO_3$, and alkoxides, particularly sodium or potassium lower, particularly $C_1$ to $C_4$, alkoxides, e.g. sodium or potassium methoxide, and tertiary amines, particularly tertiary amines including at least one tertiary nitrogen atom in a ring system, such as 1,8-diazabicyclo[5.4.0]undec-7-ene (DBU), 1,4-diazabicyclo[2.2.2]octane (DABCO), 4-(dimethylamino)pyridine (DMAP), 7-methyl-1,5,7-triazabicyclo[4.4.0]dec-5-ene (MTBD), quinuclidine, pyrrocoline, and similar materials. Base catalyst, particularly alkali metal hydroxide may be partially neutralized (or buffered) with acid, particularly fatty acids or a polybasic acid, such as phosphorus oxyacid, e.g. phosphoric acid, or reducing phosphorus oxyacids, such as phosphorous acid. The amount of catalyst may be from 0.5 to 25, more usually 2 to 20, and particularly 5 to 15, mol %, based on the initiator starting material. Calcium methoxide, $Ca(OCH_3)_2$, and potassium methoxide, $KOCH_3$, if used, are desirably used in an amount of from 3 to 18, especially from 5 to 15 mol % based on the initiator starting material, are particularly useful catalysts.

To make the compounds of the invention where the (poly) glyceryl group is a glyceryl copolymer, the synthesis may include ring-opening copolymerization with other cyclic monomers, preferably cyclic carbonates, e.g. those derived from ethylene glycol, propylene glycol and/or 1,3-propanediol, in addition to glycerol carbonate. The proportion of such other comonomer used will be chosen to provide the corresponding level of copolymeric inclusion in the chains and accordingly will typically be less than 75, more usually less than 50 and generally less than 25 mol % of the total carbonate used in the synthesis. The invention further includes a method of making a mixed poly(alkyleneoxy)/polyglycerol ether in which the initiator is reacted with glycerol carbonate and at least one other cyclic carbonate, particularly in the presence of a base catalyst.

The relative proportions of glyceryl and other units in the glyceryl copolymer can readily be determined by controlling how the monomers are supplied to the reaction. Thus, random (statistical) copolymers can be made by supplying a mixture of monomers to the reaction; block copolymers by substantially completing reaction with one monomer before another is added; taper block copolymers by adding the another monomer later than but before complete reaction of a first carbonate reagent. Sequential block, block random, and similar types of copolymeric chains can be made by combinations or ready variations on the above reaction sequences. In one preferred embodiment, acetylated glyceryl carbonate is polymerized first off of the initiator, followed by subsequent polymerization of glyceryl carbonate.

In addition to the compounds of the invention, typical synthesis reactions may generate by-products such as polyglycerol and/or polyglyceryl copolymers in side reactions initiated by species other than the intended initiator, e.g. polymerization of glycerol carbonate initiated by the free OH group of glycerol carbonate. Generally, the more monomer present in the reaction system the more likely such side polymerizations are to occur and consequently, aliquot or gradual addition of monomers over the course of the reaction reduces the amount of side product made. The polyglyceryl thickener may be separated from the side polymerization products via any of a variety of conventional separation processes including, for example, decanting, fractionation, centrifugation, and/or solvent extraction.

The synthesis reactions will be generally be carried out in a batch mode, typically by mixing the reagents in a suitable vessel and allowing them to react, usually under stirring for a suitable time. Fresh reagent, particularly glycerol carbonate, and/or catalyst may be added occasionally, at multiple intervals or continuously during the reaction (semi-batch operation). It is also possible to use continuous or semicontinuous reaction modes if desired.

Where the initiator and monomer(s) are immiscible, at the start of the reaction, the reactants form a two-phase liquid system. As the polyether (e.g., glyceryl and optional other units) chain of the etherified initiator grows, the polyethers become increasingly miscible with the monomer(s). Thus, the products and to an extent the intermediates will tend to act to compatibilize the starting materials, but when the transition to a single phase system occurs will depend on the reagents used. Reaction between components (generally) in different phases will be slower than when they are in one phase. The degree of compatibility of the intermediates may influence the relative speed of reaction as against chain length and thus influence the distribution of chain lengths in the final product. In some cases, a single phase liquid system will not form, giving rise to two different reaction products (one from each phase) that may be separated and utilized accordingly. In these cases, the reaction parameters may be adjusted accordingly to favor the formation of the desired product and minimize formation of the accompanying by product. For example, in a two-phase reaction product resulting from the reaction of methyl glucose dioleate with glycerol carbonate, one phase may comprise polyglyceryl methyl glucose dioleate with a high DPg, whereas the second phase may comprise a polyglyceryl methyl glucose dioleate with a low DPg. The two phases may be separated and collected via any of a variety of conventional separation processes including, for example, decanting, fractionation, centrifugation, and/or solvent extraction.

Typically, the reactions to make the compounds of the invention can be carried out without the need for a solvent or diluent, particularly as this will avoid any problem in isolating the desired product. However, if desired, the physical immiscibility of the starting materials may be avoided by the use of suitable inert reaction medium, solvent or diluent; however, the reaction is preferably conducted in the bulk. Suitable solvents are liquids which remain thermally stable and are inert to the reagents and products. Any solvent used will either have a relatively low vapor pressure at the reaction temperature or the reaction will be conducted under suitable containment or reflux arrangements. Suitable examples of solvents/diluents include dimethyl isosorbide, dimethylformamide, dimethylsulfoxide, and ethylene glycol and diethylene glycol diethers, e.g. dimethyl, diethyl, or dibutyl ethers.

Solvent and/or diluent may be included with the resulting polyglyceryl thickener, either by leaving reaction solvent/diluent in the product or by subsequent addition, to reduce product viscosity for transport, storage and/or subsequent use. Suitable solvents/diluents for this purpose include those mentioned above as well as glycerol carbonate (when its reactivity does not interfere with downstream product use), glycerol or, and particularly, monopropylene glycol because this may give the additional benefit of improving the molecular packing of the polyglycerol ether products at the phase interface in end use formulations. Typically such solvents/diluents will be used in amounts to give formulations having from 50 to 90, more usually 60 to 80 and particularly about 70, % by weight of the product.

The reaction temperature may be superambient, such as at least 100° C. and more usually at least 150° C. and can range up to 220° C., with the range 170 to 200° C. being generally suitable.

Typically, the reagents used to make the compounds of the invention remain liquids of low vapor pressure at reaction temperatures, so the reaction can be conveniently carried out at ambient pressure though moderately superambient pressure may be used if desired. It is unlikely that it will be desirable to use subambient pressure, but by choosing suitable involatile reagents it may be possible to carry the reaction out at moderately subambient pressure.

It is preferential to apply subambient pressure (i.e. vacuum) to the initiator during initial heating to degas and dry the initiator, as entrained oxygen will lead to discoloration of the product, and entrained water will lead to spontaneous initiation of the monomers, resulting in (co)polymers without the $Node(Hphob)_h$ functionality. It is also preferential to apply subambient pressure to the monomers prior to the reaction for degassing purposes.

To help avoid excessive color generation, particularly when reacting initiators bearing unsaturated hydrophobic moieties, the synthesis reactions will usually be carried out in a largely oxygen free atmosphere, e.g. in a nitrogen atmosphere (e.g., using a nitrogen blanket or sparge. For larger scale production, nitrogen blanketing may be less necessary and perhaps omitted.

It may be desirable to include reducing agent in the reaction to aid in control of product color. Reducing agents commonly used for this purpose, particularly in the manufacture of food or personal care products, can be used in this invention and examples include phosphorous acid ($H_3PO_3$), hypophosphorous acid ($H_3PO_2$) and borohydride (usually as sodium borohydride). Where the reducing agent is itself an acid, e.g. phosphorous or hypophosphorous acid, it will usually be present as a salt, typically an alkali metal salt. The salt may be made in situ by reaction with base, e.g. part of the basic catalyst (where used) and in this case care may be needed to ensure that sufficient base is present to neutralize the reducing acid and to act as catalyst. When used, the amount of reducing agent will typically be from 0.1 to 15 mol %, more usually 1 to 10 mol %, and particularly 2 to 7.5 mole %, based on the initiator.

Another way of reducing product color is to include particulate carbon, particularly so-called "activated carbon", or a bleaching earth, e.g. diatomaceous earth, in the reaction to absorb colored side products. When used, the amount of carbon will typically be from 0.5 to 2.5 weight % of the total reagents. Of course, this carbon or bleaching earth will generally be removed e.g. by filtration, before the products are included in end use formulations. Activated carbon and a reducing agent may be used together in the reaction if desired. Further color improvement can be achieved by treatment of the reaction product with particulate carbon, particularly activated carbon, or bleaching earth, typically at from 0.5 to 2.5 weight % of the product, or by bleaching the product of the reaction, e.g. with a peroxide based bleach, generally after removal of any activated carbon or bleaching earth.

According to certain embodiments of the invention, polyglyceryl thickener is used in a personal care composition. The personal care composition may comprise, consists of, or consist essentially of a base and the polyglyceryl thickener. The base comprises water, surfactant, and optionally, any of various ingredients typically used in personal care products.

Any amounts of polyglyceryl thickeners suitable to increase viscosity of compositions of the present invention may be used according to the present methods. For example, polyglyceryl thickener may be included in an amount in the personal care composition sufficient to increase the Zero Shear Viscosity of the base by about 100 cP or more (when tested according to the Zero Shear Viscosity Test, described below). In certain preferred embodiments, the compositions of the present invention comprise an amount of polyglyceryl thickener sufficient to increase the Zero Shear Viscosity of the base by about 200 cP or more, more preferably by about 300 cP or more, more preferably by about 500 cP or more, more preferably by about 1000 cP or more. The increases in viscosity specified above are as when compared with a composition which has water substituted for the polyglyceryl thickener.

According to certain embodiments, the polyglyceryl thickener is used in a concentration from greater than about 0.1% to about 15% by weight in the composition. Preferably, the polyglyceryl thickener is in a concentration from about 0.1 to about 10%, more preferably from about 0.1% to about 5%, even more preferably from about 0.2% to about 4%, even more preferably from about 0.5% to about 4%, and most preferably from about 1% to about 4% in the composition.

Compositions useful in the present invention may also include any of a variety of surfactants. The surfactants may be anionic, zwitterionic (i.e. amphoteric or betaine), nonionic, or cationic, examples of which are detailed below. Where applicable, chemicals are specified according to their International Nomenclature of Cosmetic Ingredients (INCI) names.

According to certain embodiments, suitable anionic surfactants include those selected from the following classes of surfactants: alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof. Examples of certain preferred anionic surfactants include:

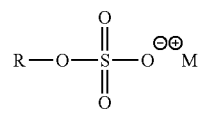

Alkyl sulfates where R=$C_8$-$C_{24}$ alkyl (linear or branched, saturated or unsaturated) or mixtures thereof and $M^+$=monovalent cation. Examples include Sodium Lauryl Sulfate (R=$C_{12}$ alkyl, $M^+$=$Na^+$), Ammonium Lauryl Sulfate (R=$C_{12}$ alkyl, $M^+$=$NH_3^+$), and Sodium Coco-Sulfate (R=coconut alkyl, $M^+$=$Na^+$);

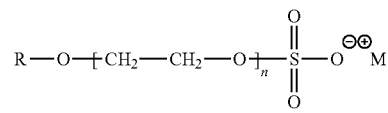

Alkyl ether sulfates where R=$C_8$-$C_{24}$ alkyl (linear or branched, saturated or unsaturated) or mixtures thereof, n=1-12, and $M^+$=monovalent cation. Examples include Sodium Laureth Sulfate (R=$C_{1-2}$ alkyl, $M^+$=$Na^+$, n=1-3), Ammonium Laureth Sulfate (R=$C_{1-2}$ alkyl, $M^+$=$NH_3^+$, n=1-3), and Sodium Trideceth Sulfate (R=$C_{13}$ alkyl, $M^+$=$Na^+$, n=1-4);

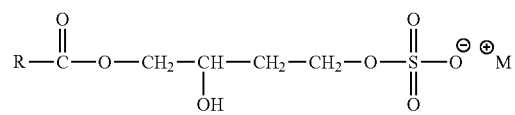

Alkyl monoglyceride sulfates where R=$C_8$-$C_{24}$ alkyl (linear or branched, saturated or unsaturated) or mixtures thereof and $M^+$=monovalent cation. Examples include Sodium Cocomonoglyceride Sulfate (RCO=coco acyl, $M^+$=$Na^+$) and Ammonium Cocomonoglyceride Sulfate (RCO=coco acyl, $M^+$=$NH_3^+$);

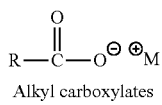
Alkyl carboxylates where R=$C_8$-$C_{24}$ alkyl (linear or branched, saturated or unsaturated) or mixtures thereof and $M^+$=monovalent cation. Examples include Sodium Laurate (R=$C_{11}H_{23}$, $M^+$=$Na^+$) and Potassium Myristate (R=$C_{13}H_{27}$, $M^+$=$K^+$);

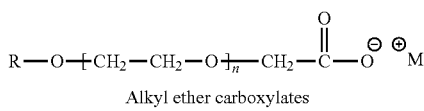
Alkyl ether carboxylates where R=$C_8$-$C_{24}$ alkyl (linear or branched, saturated or unsaturated) or mixtures thereof, n=1-20, and $M^+$=monovalent cation. Examples include Sodium Laureth-13 Carboxylate (R=$C_{1-2}$ alkyl, $M^+$=$Na^+$, n=13), and Sodium Laureth-3 Carboxylate (R=$C_{1-2}$ alkyl, $M^+$=$Na^+$, n=3);

Alpha olefin sulfonates prepared by sulfonation of long chain alpha olefins. Alpha olefin sulfonates consist of mixtures of alkene sulfonates,

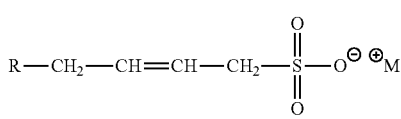

where R=$C_8$-$C_{18}$ alkyl or mixtures thereof and $M^+$=monovalent cation, and hydroxyalkyl sulfonates,

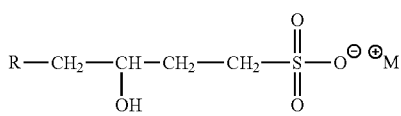

where R=$C_4$-$C_{18}$ alkyl or mixtures thereof and $M^+$=monovalent cation. Examples include Sodium C12-14 Olefin Sulfonate (R=$C_8$-$C_{10}$ alkyl, $M^+$=$Na^+$) and Sodium C14-16 Olefin Sulfonate (R=$C_{10}$-$C_{12}$ alkyl, $M^+$=$Na^+$);

Alkyl sulfonates:

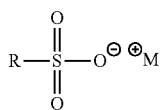

where R=$C_8$-$C_{24}$ alkyl (linear or branched, saturated or unsaturated) or mixtures thereof and $M^+$=monovalent cation. Examples include Sodium C13-17 Alkane Sulfonate (R=$C_{13}$-$C_{17}$ alkyl, $M^+$=$Na^+$) and Sodium C14-17 Alkyl Sec Sulfonate (R=$C_{14}$-$C_{17}$ alkyl, $M^+$=$Na^+$);

Alkylaryl sulfonates where R=$C_6$-$C_{18}$ alkyl (linear or branched, saturated or unsaturated) or mixtures thereof and $M^+$=monovalent cation. Examples include Sodium Deceylbenzenesulfonate (R=$C_{10}$) alkyl, $M^+$=$Na^+$) and Ammonium Dodecylbenzensulfonate (R=$C_{12}$ alkyl, $M^+$=$NH_3^+$);

Alkyl glyceryl ether sulfonates:

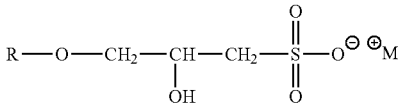

where R=$C_8$-$C_{24}$ alkyl (linear or branched, saturated or unsaturated) or mixtures thereof and $M^+$=monovalent cation, such as Sodium Cocoglyceryl Ether Sulfonate (R=coco alkyl, $M^+$=$Na^+$);

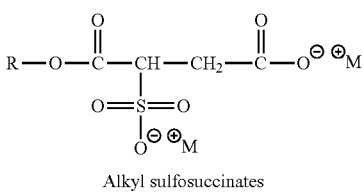
Alkyl sulfosuccinates

Where R=$C_8$-$C_{20}$ alkyl (linear or branched, saturated or unsaturated) or mixtures thereof and $M^+$=monovalent cation, such as Disodium Lauryl Sulfosuccinate (R=lauryl, $M^+$=$Na^+$).

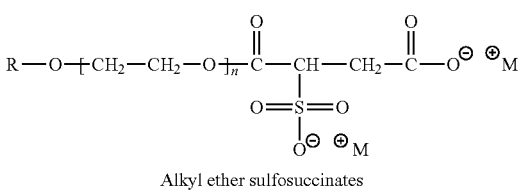
Alkyl ether sulfosuccinates

Where R=$C_8$-$C_{20}$ alkyl (linear or branched, saturated or unsaturated) or mixtures thereof, n=1-12, and $M^+$=monovalent cation, such as Disodium Laureth Sulfosuccinate (R=lauryl, n=1-4, and $M^+$=$Na^+$)

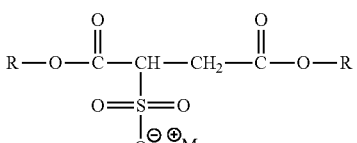
Dialkyl sulfosuccinates

Where R=$C_6$-$C_{20}$ alkyl (linear or branched, saturated or unsaturated) or mixtures thereof and $M^+$=monovalent cation, such as Diethylhexyl Sodium Sulfosuccinate (R=2-ethylhexyl, $M^+$=$Na^+$).

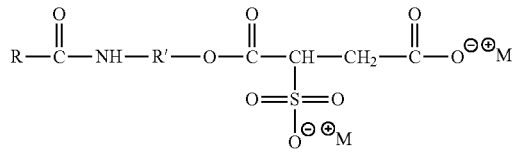

Alkylamidoalkyl sulfosuccinates

Where R=$C_8$-$C_{20}$ alkyl (linear or branched, saturated or unsaturated) or mixtures thereof, R'=$C_2$-$C_4$ alkyl (linear or branched), and $M^+$=monovalent cation, such as Disodium Cocamido MIPA-Sulfosuccinate (RCO=coco acyl, R'=isopropyl, $M^+$=$Na^+$).

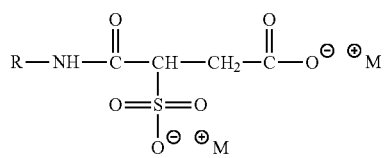

Alkyl sulfosuccinamates

Where R=$C_8$-$C_{20}$ alkyl (linear or branched, saturated or unsaturated) or mixtures thereof and $M^+$=monovalent cation, such as Disodium Stearyl Sulfosuccinamate (R=stearyl, $C_{18}H_{37}$, $M^+$=$Na^+$).

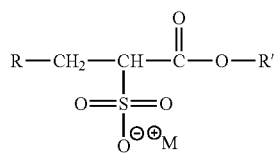

α-Sulfo fatty acid esters

Where R=$C_6$-$C_{16}$ alkyl (linear or branched, saturated or unsaturated) or mixtures thereof, R'=$C_1$-$C_4$ alkyl, and $M^+$=monovalent cation, such as Sodium Methyl 2-Sulfolaurate (R=$C_{10}H_{21}$, R'=methyl, $CH_3$, and $M^+$=$Na^+$).

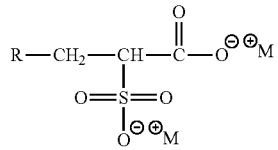

α-Sulfo fatty acid salts

Where R=$C_6$-$C_{16}$ alkyl (linear or branched, saturated or unsaturated) or mixtures thereof, $M^+$=monovalent cation, such as Disodium 2-Sulfolaurate (R=$C_{10}H_{21}$, $M^+$=$Na^+$).

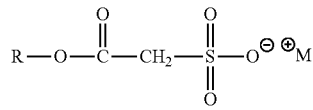

Alkyl sulfoacetates

Where R=$C_8$-$C_{18}$ alkyl (linear or branched, saturated or unsaturated) or mixtures thereof, $M^+$=monovalent cation, such as Sodium Lauryl Sulfoacetate (R=lauryl, $C_{12}H_{25}$, $M^+$=$Na^+$).

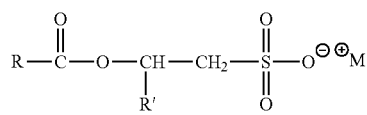

Acyl isethionates

Where RCO=$C_8$-$C_{20}$ acyl (linear or branched, saturated or unsaturated) or mixtures thereof, R'=H or $CH_3$, $M^+$=monovalent cation, such as Sodium Cocoyl Isethionate (RCO=coco acyl, R'=H, $M^+$=$Na^+$) and Sodium Lauroyl Methyl Isethionate (RCO=lauroyl, R'=$CH_3$, $M^+$=$Na^+$).

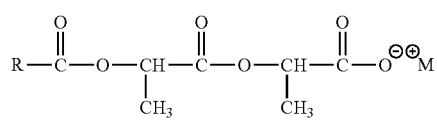

Acyl lactylates

Where RCO=$C_8$-$C_{20}$ acyl (linear or branched, saturated or unsaturated) or mixtures thereof, $M^+$=monovalent cation, such as Sodium Lauroyl Lactylate (RCO=lauroyl, $M^+$=$Na^+$).

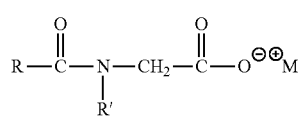

Acyl glycinates and acyl sarcosinates

Where RCO=$C_8$-$C_{20}$ acyl (linear or branched, saturated or unsaturated) or mixtures thereof, R'=H (glycinate) or $CH_3$ (sarcosinate), $M^+$=monovalent cation, such as Sodium Cocoyl Glycinate (RCO=coco acyl, R'=H, $M^+$=$Na^+$), Ammonium Cocoyl Sarcosinate (RCO=coco acyl, R'=$CH_3$, $M^+$=$NH_4^+$) and Sodium Lauroyl Sarcosinate (RCO=lauroyl, R'=$CH_3$, $M^+$=$Na^+$).

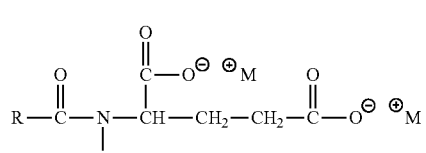

Acyl glutamates

Where RCO=$C_8$-$C_{20}$ acyl (linear or branched, saturated or unsaturated) or mixtures thereof, R'=H or $CH_3$, $M^+$=monovalent cation, such as Disodium Cocoyl Glutamate (RCO=coco acyl, R'=H, M⁺=Na⁺) and Disodium Lauroyl Glutamate (RCO=lauroyl, R'=H, M⁺=Na⁺).

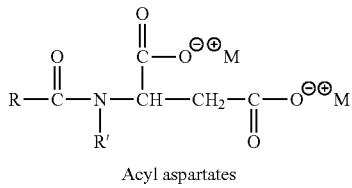

Acyl aspartates

Where RCO=$C_8$-$C_{20}$ acyl (linear or branched, saturated or unsaturated) or mixtures thereof, R'=H or $CH_3$, M⁺=monovalent cation, such as Disodium N-Lauroyl Aspartate (RCO=lauroyl, R'=H, M⁺=Na⁺).

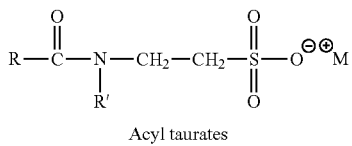

Acyl taurates

Where RCO=$C_6$-$C_{20}$ acyl (linear or branched, saturated or unsaturated) or mixtures thereof, R'=H or $CH_3$, M⁺=monovalent cation, such as Disodium Cocoyl Glutamate (RCO=coco acyl, R'=H, M⁺=Na⁺) and Disodium Lauroyl Glutamate (RCO=lauroyl, R'=H, M⁺=Na⁺).

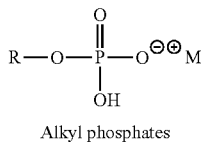

Alkyl phosphates

Where R=$C_6$-$C_{20}$ alkyl (linear or branched, saturated or unsaturated) or mixtures thereof and M⁺=monovalent cation, such as Potassium Lauryl Phosphate (R=lauryl, $C_{12}H_{25}$, M⁺=K⁺) and Potassium C12-13 Alkyl Phosphate (R=$C_{12}$-$C_{13}$ alkyl, M⁺=K⁺)

Anionic derivatives of alkyl polyglucosides (APGs), including: Sodium Lauryl Glucoside Carboxylate, Disodium Coco-Glucoside Citrate, Sodium Coco-Glucoside Tartrate, Disodium Coco-Glucoside Sulfosuccinate, Sodium Cocoglucosides Hydroxypropylsulfonate, Sodium Decylglucosides Hydroxypropylsulfonate, Sodium Laurylglucosides Hydroxypropylsulfonate, Sodium Hydroxypropylsulfonate Cocoglucoside Crosspolymer, Sodium Hydroxypropylsulfonate Decylglucoside Crosspolymer, Sodium Hydroxypropylsulfonate Laurylglucoside Crosspolymer; and anionic polymeric APG derivatives, such as those described in O'Lenick, U.S. Pat. Nos. 7,507,399; 7,375,064; and 7,335,627), and combinations of two or more thereof, and the like.

Any of a variety of amphoteric surfactants are suitable for use in the present invention. As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and alkylamidoalkyl betaines. The amphoteric surfactants are disclosed herein with a counterion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions. Examples of amphoteric surfactants suitable for use in the present invention include, but are not limited to, amphocarboxylates such as alkylamphoacetates (mono or di); alkyl betaines; alkylamidoalkyl betaines; alkylamidoalkyl sultaines; alkylamphophosphates; phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di)); N-alkyl β-aminoproprionic acids; alkylpolyamino carboxylates; and mixtures thereof. Specific examples include:

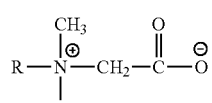

Alkyl betaines where R=$C_8$-$C_{24}$ alkyl (saturated or unsaturated) or mixtures thereof. Examples include Coco-Betaine (R=coco alkyl), Lauryl Betaine (R=lauryl, $C_{12}H_{25}$), and Oleyl Betaine (R=oleyl, $C_{18}H_{35}$).

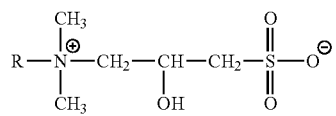

Alkyl hydroxysultaines where R=$C_8$-$C_{24}$ alkyl (saturated or unsaturated) or mixture thereof. Examples include Coco-Hydroxysultaine (R=coco alkyl) and Lauryl Hydroxysultaine (R=lauryl, $C_{12}H_{25}$).

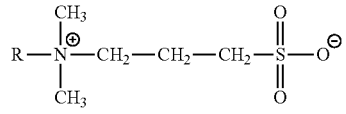

Alkyl sultaines where R=$C_8$-$C_{24}$ alkyl (saturated or unsaturated) or mixture thereof. Examples include Lauryl Sultaine (R=lauryl, $C_{12}H_{25}$) and Coco-Sultaine (R=coco alkyl).

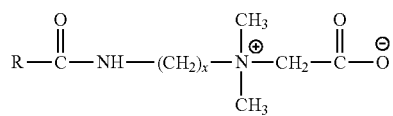

Alkylamidoalkyl betaines where RCO=$C_6$-$C_{24}$ acyl (saturated or unsaturated) or mixtures thereof and x=1-4. Examples include Cocamidoethyl Betaine (RCO=coco acyl, x=2), Cocamidopropyl Betaine (RCO=coco acyl, x=3), Lauramidopropyl Betaine (RCO=lauroyl, and x=3), Myristamidopropyl Betaine (RCO=myristoyl, and x=3), Soyamidopropyl Betaine (R=soy acyl, x=3), and Oleamidopropyl Betaine (RCO=oleoyl, and x=3).

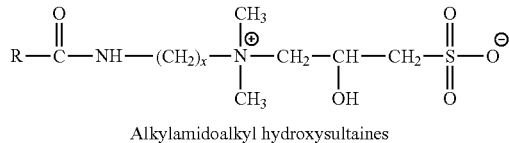

Alkylamidoalkyl hydroxysultaines where RCO=$C_6$-$C_{24}$ acyl (saturated or unsaturated) or mixtures thereof. Examples include Cocamidopropyl Hydroxysultaine (RCO=coco acyl, x=3), Lauramidopropyl Hydroxysultaine (RCO=lauroyl, and x=3), Myristamidopropyl Hydroxysultaine (RCO=myristoyl, and x=3), and Oleamidopropyl Hydroxysultaine (RCO=oleoyl, and x=3).

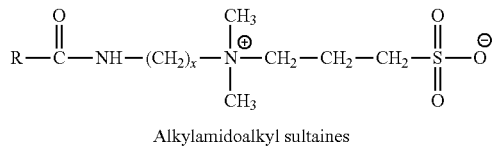

Alkylamidoalkyl sultaines where RCO=$C_6$-$C_{24}$ acyl (saturated or unsaturated) or mixtures thereof. Examples include Cocamidopropyl Sultaine (RCO=coco acyl, x=3), Lauramidopropyl Sultaine (RCO=lauroyl, and x=3), Myristamidopropyl Sultaine (RCO=myristoyl, and x=3), Soyamidopropyl Betaine (RCO=soy acyl, x=3), and Oleamidopropyl Betaine (RCO=oleoyl, and x=3).

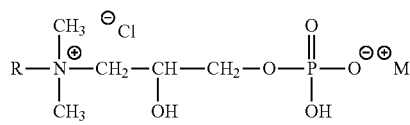

Alkyl phosphobetaines where R=$C_6$-$C_{24}$ alkyl (saturated or unsaturated) or mixtures thereof and M$^+$=monovalent cation, such as Sodium Coco PG-Dimonium Chloride Phosphate, where R=coco alkyl and M$^+$=Na$^+$.

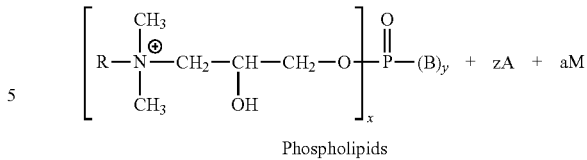

Phospholipids where R=$C_6$-$C_{24}$ alkyl (saturated or unsaturated) or mixtures thereof, x=1-3 or mixtures thereof, x+y=3, z=x, a=0 to 2, B=O$^-$, or OM, A=Anion, and M=Cation (refer to U.S. Pat. Nos. 5,215,976; 5,286,719; 5,648,348; and 5,650,402), such as Sodium Coco PG-Dimonium Chloride Phosphate, where R=coco alkyl, x=2, B=O$^-$, y=1, z=1, A=Cl$^-$, a=1, and M=Na$^+$.

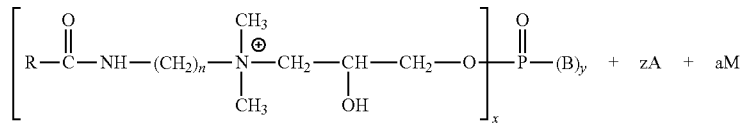

Phospholipids where RCO=$C_6$-$C_{24}$ acyl (saturated or unsaturated) or mixtures thereof, n=1-4, x=1-3 or mixtures thereof, x+y=3, z=x, a=0 to 2, B=O$^-$ or OM, A=anion, and M=cation (refer to U.S. Pat. Nos. 5,215,976; 5,286,719; 5,648,348; and 5,650,402). Examples include Cocamidopropyl PG-Dimonium Chloride Phosphate (RCO=coco acyl, n=3, x=3, z=3, A=Cl$^-$, B and M are absent, y=0, and a=0) and Myristamidopropyl PG-Dimonium Chloride Phosphate (RCO=myristoyl, n=3, x=3, z=3, A=Cl$^-$, B and M are absent, y=0, and a=0).

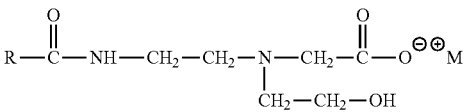

Alkyl amphoacetates where RCO=$C_6$-$C_{24}$ acyl (saturated or unsaturated) or mixtures thereof and M$^+$=monovalent cation. Examples include Sodium Lauroamphoacetate (RCO=lauroyl and M$^+$=Na$^+$) and Sodium Cocoamphoacetate (RCO=coco acyl and M$^+$=Na$^+$).

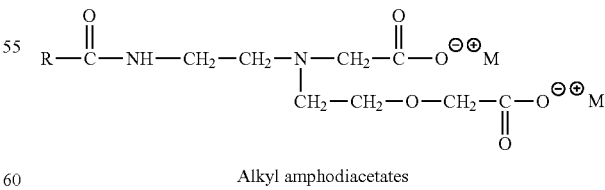

Alkyl amphodiacetates where RCO=$C_6$-$C_{24}$ acyl (saturated or unsaturated) or mixtures thereof and M$^+$=monovalent cation. Examples include Disodium Lauroamphodiacetate (RCO=lauroyl and M=Na$^+$) and Disodium Cocoamphodiacetate (RCO=coco acyl and M=Na$^+$).

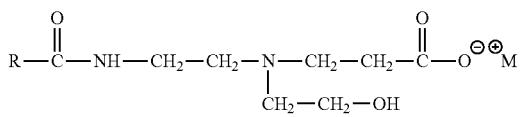

Alkyl amphopropionates where RCO=$C_6$-$C_{24}$ acyl (saturated or unsaturated) or mixtures thereof and $M^+$=monovalent cation. Examples include Sodium Lauroamphopropionate (RCO=lauroyl and $M^+$=$Na^+$) and Sodium Cocoamphopropionate (RCO=coco acyl and $M^+$=$Na^+$).

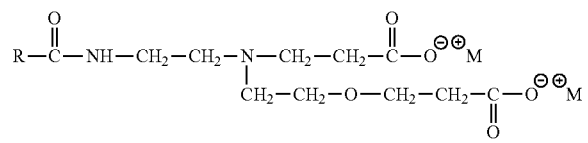

Alkyl amphodipropionates where RCO=$C_6$-$C_{24}$ acyl (saturated or unsaturated) or mixtures thereof and $M^+$=monovalent cation. Examples include Disodium Lauroamphodipropionate (RCO=lauroyl and $M^+$=$Na^+$) and Disodium Cocoamphodipropionate (RCO=coco acyl and $M^+$=$Na^+$).

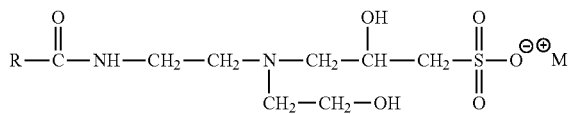

Alkyl amphohydroxypropylsulfonates where RCO=$C_6$-$C_{24}$ acyl (saturated or unsaturated) or mixtures thereof and $M^+$=monovalent cation, such as Sodium Lauroamphohydroxypropylsulfonate (RCO=lauroyl and $M^+$=$Na^+$) and Sodium Cocoamphohydroxypropylsulfonate (RCO=coco acyl and $M^+$=$Na^+$).

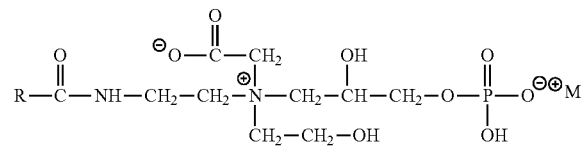

Alkyl amphohydroxyalkylphosphates where RCO=$C_6$-$C_{24}$ acyl (saturated or unsaturated) or mixtures thereof and $M^+$=monovalent cation, such as Sodium Lauroampho PG-Acetate Phosphate (RCO=lauroyl and $M^+$=$Na^+$).

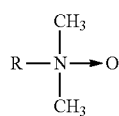

Alkyl amine oxides where R=$C_6$-$C_{24}$ alkyl (saturated or unsaturated) or mixtures thereof. Examples include Cocamine Oxide (R=coco alkyl) and Lauramine Oxide (RCO=lauryl).

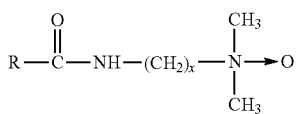

Alkylamidoalkyl amine oxides where RCO=$C_6$-$C_{24}$ acyl (saturated or unsaturated) or mixtures thereof and x=1-4. Examples include Cocamidopropylamine Oxide (RCO=coco acyl, x=3) and Lauramidopropylamine Oxide (RCO=lauroyl, x=3), and combinations of two or more thereof, and the like.

Any of a variety of ethoxylated nonionic surfactants are suitable for use in the present invention. Examples of suitable nonionic surfactants include, but are not limited to: fatty alcohol, fatty acid, or fatty amide ethoxylates; monoglyceride ethoxylates; sorbitan ester ethoxylates; mixtures thereof; and the like. Certain preferred ethoxylated nonionic surfactants include polyethyleneoxy derivatives of polyol esters, wherein the polyethyleneoxy derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerol, pentaerythritol and mixtures thereof, (2) contains an average of from about 10 to about 120, and preferably about 20 to about 80 ethyleneoxy units; and (3) has an average of about 1 to about 3 fatty acid residues per mole of polyethyleneoxy derivative of polyol ester. Examples of such preferred polyethyleneoxy derivatives of polyol esters include, but are not limited to PEG-80 Sorbitan Laurate and Polysorbate 20.

While the compositions may comprise ethoxylated materials as described above in accord with certain embodiments, according to certain other embodiments, the compositions of the present invention are substantially free of ethoxylated materials. As used herein, the term "substantially free of ethoxylated materials" means a composition that comprises less than 1% by weight of total ethoxylated materials. In preferred embodiments, compositions that are substantially free of ethoxylated materials comprise less than 0.5%, more preferably less than 0.1%, and even more preferable are free of, ethoxylated materials.

As used herein, the term "ethoxylated material" means a material comprising one or more moieties derived from or prepared by the ring-opening oligomerization or polymerization of ethylene oxide and/or comprising one or more oxyethylene (—$CH_2CH_2O$—) moieties. Examples of ethoxylated materials include, but are not limited to, ethoxylated surfactants, emulsifiers, solubilizers, rheology modifiers, conditioning agents, preservatives, and the like, such as, for example anionic surfactants: polyoxyethylene alkyl ether sulfates (a.k.a. alkyl ether sulfates), polyoxyethylene alkyl ether carboxylates (a.k.a. alkyl ether carboxylates), polyoxyethylene alkyl ether sulfosuccinate esters; nonionic surfactants, emulsifiers, and solubilizers: polyoxyethylene alkyl ethers and esters, polysorbates, ethoxylated sorbitan fatty acid esters, ethoxylated glyceryl fatty acid esters, poloxamers; rheology modifiers: polyoxyethylene esters (e.g. PEG-150 Distearate), ethyoxylated alkyl glucoside esters (e.g. PEG-120 Methyl Glucose Trioleate), acrylic copolymers with ethoxylated associative macromonomers (e.g. Acrylates/Steareth-20 Methacrylate Copolymer), ethoxylated cellulose ethers (e.g. Hydroxyethylcellulose); conditioning agents: ethoxylated polyquaterniums (e.g. Polyquaternium-10); and the like.

Any of a variety of non-ethoxylated nonionic surfactants are also suitable for use in the present invention. Examples of suitable non-ethoxylated nonionic surfactants include alkyl polyglucosides, alkyl polypentosides, polyglyceryl esters, polyglyceryl ethers, polyglyceryl sorbitan fatty acid esters, sucrose esters, and sorbitan esters, and combinations of two or more thereof and the like. Certain preferred non-ethoxylated nonionic surfactants include $C_8$-$C_{18}$ polyglyceryl monoesters (e.g. polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and combinations of two or more thereof) and $c_8$-$c_{18}$ polyglyceryl monoethers (e.g. polyglyceryl-4 lauryl ether, polyglyceryl-10 lauryl ether)

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl glucosides comprise from about 1 to about 6 glucose residues per molecule of alkyl glucoside. A preferred glucoside is Decyl Glucoside, which is the condensation product of decyl alcohol with a glucose polymer and is available commercially from Cognis Corporation of Ambler, Pa. under the trade name, "Plantaren 2000N UP." Other examples include Coco-Glucoside and Lauryl Glucoside.

The compositions of the present invention may comprise any of a variety of additional other ingredients used conventionally in healthcare/personal care compositions ("personal care components"). These other ingredients nonexclusively include one or more, pearlescent or opacifying agents, thickening agents, emollients, secondary conditioners, humectants, chelating agents, actives, exfoliants, and additives which enhance the appearance, feel and fragrance of the compositions, such as colorants, fragrances, preservatives, pH adjusting agents, and the like.

Compositions useful in the present invention may also include any of a variety of conventional thickening agents. Examples of such thickening agents include: electrolytes (e.g. Sodium Chloride, Ammonium Chloride, Magnesium Chloride); naturally-derived polysaccharides (e.g. Xanthan Gum, Dehydroxanthan Gum, *Cyamopsis Tetragonoloba* (Guar) Gum, *Cassia* Gum, *Chondrus Crispus* (Carrageenan) Gum, Alginic Acid and alginate gums (Algin, Calcium Alginate, etc.), Gellan Gum, Pectin, Microcrystalline Cellulose); derivatives of natural polysaccharides (e.g. Hydroxyethylcellulose, Ethyl Hydroxyethylcellulose, Cetyl Hydroxyethylcellulose, Methylcellulose, Hydroxypropylcellulose, Sodium Carboxymethylcellulose, Hydroxypropyl Methylcellulose, Hydroxypropyl Guar, Carboxymethyl Hydroxypropyl Guar, C18-22 Hydroxylalkyl Hydroxypropyl Guar); alkali-swellable emulsion (ASE) polymers (e.g. Acrylates Copolymer, available under the trade name Carbopol® AQUA SF-1 from Noveon Consumer Specialties, Brecksville, Ohio, and Acrylates Copolymer available under the trade name Aculyn™ 33 from Dow Personal Care, Spring House, PA); hydrophobically-modified alkali-swellable emulsion (HASE) polymers (e.g. Acrylates/Steareth-20 Methacrylate Copolymer, Acrylates/Steareth-20 Methacrylate Crosspolymer, and Acrylates/Ceteth-20 Itaconate Copolymer); hydrophobically-modified acid-swellable emulsion polymers (e.g. Acrylates/Aminoacrylates/C10-30 Alkyl PEG-20 Itaconate Copolymer and Polyacrylate-1 Crosspolymer); hydrophobically-modified acrylate crosspolymers, such as Acrylates C10-30 Alkyl Acrylates Crosspolymer, available under the trade name Carbopol® 1382 from Lubrizol Corp., Brecksville, Ohio; and hydrophobic non-ethoxylated micellar thickeners (e.g. Glyceryl Oleate, Cocamide MIPA, Lauryl Lactyl Lactate, or Sorbitan Sesquicaprylate).

Any of a variety of skin and/or hair conditioning agents are suitable for use in this invention. Examples include: cationic surfactants (e.g. Cetrimonium Chloride, Stearamidopropyl Dimethylamine, Distearyldimonium Chloride, Lauryl Methyl Gluceth-10 Hydroxypropyldimonium Chloride); cationic polymers (e.g. cationically-modified polysaccharides, including Polyquaternium-10, Polyquaternium-24, Polyquaternium-67, Starch Hydroxypropyltrimonium Chloride, Guar Hydroxypropyltrimonium Chloride, and Hydroxypropyl Guar Hydroxypropyltrimonium Chloride, and cationic polymers derived from the (co)polymerization of ethylenically-unsaturated cationic monomers with optional hydrophilic monomers, including Polyquaternium-5, Polyquaternium-6, Polyquaternium-7, Polyquaternium-11, Polyquaternium-14, Polyquaternium-15, Polyquaternium-28, Polyquaternium-39, Polyquaternium-44; Polyquaternium-76); silicones and silicone derivatives (e.g. Dimethicone and derivatives thereof, such as alkyl-, polyalkyleneoxy-, cationically-, anionically-modified dimethicone (co)polymers); and emollients (e.g. Caprylic/Capric Triglycerides, Mineral Oil, Petrolatum, Di-PPG-2 Myreth-10 Adipate).

Any of a variety of humectants, which are capable of providing moisturization and conditioning properties to the personal cleansing composition, are suitable for use in the present invention. Examples of suitable humectants nonexclusively include polyols, such as Glycerin, Propylene Glycol, 1,3-Propanediol, Butylene Glycol, Hexylene Glycol, polyglycerinso (e.g. Polyglycerin-3, Polyglyceryn-6, Polyglycerin-10), polyethylene glycols (PEGs), and polyoxyethylene ethers of α-methyl glucose, such as Methyl Gluceth-10 and Methyl Gluceth-20.

Examples of suitable chelating agents include those which are capable of protecting and preserving the compositions of this invention. Preferably, the chelating agent is ethylenediamine tetraacetic acid ("EDTA"), and more preferably is Tetrasodium EDTA or Tetrasodium Glutamate Diacetate.

Suitable preservatives include, for example, organic acids, parabens (e.g. Methylparaben, Ethylparaben, Propylparaben, Butylparaben, Isobutylparaben), quaternary ammonium species (e.g. Quaternium-15), phenoxyethanol, DMDM hydantoin, Diazolidinyl Urea, Imidazolidinyl Urea, Iodopropynyl Butylcarbamate, Methylisothazolinone, Methylchloroisothizaolinone, Benzyl Alcohol, Caprylyl Glycol, Decylene Glycol, Ethylhexylglycerin, and Gluconolactone. Preferred are organic acid preservatives that comprise at least one carboxylic acid moiety and are capable of preserving a composition of the present invention against microbial contamination Examples of suitable organic acids include Benzoic Acid and alkali metal and ammonium salts thereof (e.g. Sodium Benzoate and the like), Sorbic Acid and alkali metal and ammonium salts thereof (e.g. Potassium Sorbate and the like), p-Anisic Acid and alkali metal and ammonium salts thereof, Salicylic Acid and alkali metal and ammonium salts thereof, and the like. In certain preferred embodiments, the organic acid preservative comprises Benzoic Acid/Sodium Benzoate, Sorbic Acid/Potassium Sorbate, or combinations thereof.

The pH of the composition may be adjusted to the appropriate value using any number of cosmetically acceptable pH adjusters, including: alkali metal and ammonium hydroxides (e.g. Sodium Hydroxide, Potassium Hydroxide), alkali metal and ammonium carbonates (e.g. Potassium Carbonate), organic acids (e.g. Citric Acid, Acetic Acid, Glycolic Acid, Lactic Acid, Malic acid, Tartaric Acid), and inorganic acids (e.g. Hydrochloric Acid, Phosphoric Acid), and the like.

The polyglyceryl thickener, optional monomeric surfactants and optional other components of the composition may be combined according to the present invention via any conventional methods of combining two or more fluids or solids. For example, one or more compositions comprising, consisting essentially of, or consisting of at least one polyglyceryl thickener and one or more compositions comprising, consisting essentially of, or consisting of water, monomeric surfactants or suitable ingredients may be combined by pouring, mixing, adding dropwise, pipetting, pumping, and the like, one of the compositions comprising the polyglyceryl thickener into or with the other in any order using any conventional equipment such as a mechanically stirred propeller, paddle, and the like.

The methods of the present invention may further comprise any of a variety of steps for mixing or introducing one or more of the optional components described hereinabove with or into a composition comprising a polyglyceryl thickener either before, after, or simultaneously with the combining step described above. While in certain embodiments, the order of mixing is not critical, it is preferable, in other embodiments, to pre-blend certain components, such as the fragrance and the nonionic surfactant before adding such components into a composition comprising the polyglyceryl thickener.

Applicants have recognized that n accord with certain embodiments, the compositions of the present invention are suitable for generating desirable amounts of foam. According to certain embodiments, the compositions of the present invention exhibit foam values of about 75 mL or greater as measured in accord with the Formulation Foam Test. According to certain preferred embodiments, the compositions of the present invention exhibit foam values of about 100 mL or greater, more preferably about 125 mL or greater, and even more preferably about 150 mL or greater as measured in accord with the Formulation Foam Test.

The compositions useful in the present invention involve formulations suitable for administering to the target tissues, such as mammalian skin such as human skin. In one embodiment, the composition comprises a polyglyceryl thickener and a base, preferably a cosmetically-acceptable base. As used herein, the term "cosmetically-acceptable base" means a base that is suitable for use in contact with the skin without undue toxicity, incompatibility, instability, irritation, allergic response, and the like. This term is not intended to limit the base for use solely as a cosmetic (e.g., the ingredient/product can be used as a pharmaceutical).

The compositions may be made into a wide variety of product types that include but are not limited to cleansing liquid washes, gels, sticks, sprays, solid bars, shampoos, pastes, foams, powders, mousses, shaving creams, wipes, patches, wound dressing and adhesive bandages, hydrogels, films and make-up such as foundations, mascaras, and lipsticks. These product types may comprise several types of cosmetically-acceptable carriers including, but not limited to solutions, emulsions (including microemulsions and nanoemulsions), suspensions, gels, and solids. The following are non-limitative examples of such carriers. Other carriers can be formulated by those of ordinary skill in the art.

The compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include: polyglycerols, propylene glycol, polyethylene glycol (200, 600), polypropylene glycol (425, 2025), glycerol, 1,2,4-butanetriol, sorbitol esters, 1,2,6-hexanetriol, ethanol, and mixtures thereof. In certain preferred embodiments, the compositions of the present invention are aqueous solutions comprising from about 50% to about 99% by weight of water.

According to certain embodiments, compositions useful in the subject invention may be formulated as a solution comprising an emollient. Such compositions preferably contain from about 2% to about 50% of an emollient(s). As used herein, "emollients" refer to materials used for the prevention or relief of dryness, as well as for the protection of the skin. A wide variety of suitable emollients are known and may be used herein. A lotion can be made from such a solution. Lotions typically comprise from about 1% to about 20% (e.g., from about 5% to about 10%) of an emollient(s) and from about 50% to about 90% (e.g., from about 60% to about 80%) of water.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents.

The present compositions may be of varying phase compositions, but are preferably aqueous solutions or otherwise include an exterior aqueous phase (e.g., aqueous phase is the most exterior phase of the composition). As such, compositions of the present invention may be formulated to be oil-in-water emulsions that are shelf-stable in that the emulsion does not lose phase stability or "break" when kept at standard conditions (22 degrees Celsius, 50% relative humidity) for a week or more after it is made.

In certain embodiments, the compositions produced via the present invention are preferably used as or in healthcare products for treating or cleansing at least a portion of a mammalian body, for example, the human body. Examples of certain preferred personal care products include various products suitable for application to the skin, hair, oral and/or perineal region of the body, such as shampoos, hand, face, and/or body washes, bath additives, gels, lotions, creams, and the like. As discussed above, applicants have discovered unexpectedly that the instant methods provide personal care products having reduced irritation to the skin and/or eyes and, in certain embodiments one or more of desirable properties such as flash foaming characteristics, rheology, and functionality, even at high surfactant concentrations. Such products may further include a substrate onto which a composition is applied for use on the body. Examples of suitable substrates include a wipe, pouf, sponge, and the like as well as absorbent articles, such as a bandage, sanitary napkin, tampon, and the like.

The present invention provides methods of treating and/or cleansing the human body comprising contacting at least a portion of the body with a composition of the present invention. Certain preferred methods comprising contacting mammalian skin, hair and/or vaginal region with a composition of the present invention to cleanse such region and/or treat such region for any of a variety of conditions including, but not limited to, acne, wrinkles, dermatitis, dryness, muscle pain, itch, and the like. In certain preferred embodiments, the contacting step comprises applying a composition of the present invention to human skin, hair or vaginal region. The cleansing methods of the present invention may further comprise any of a variety of additional, optional steps associated conventionally with cleansing hair and skin including, for example, lathering, rinsing steps, and the like.

EXAMPLES

The following Test Methods and Procedures were used:

Average Degree of Glyceryl Polymerization Measurement Procedure

The average degree of glyceryl polymerization $DP_g$ for a subject polyglyceryl thickener was obtained using NMR techniques as follows: $^1H$ NMR spectra were obtained in deuterated dimethyl sulfoxide (DMSO-D6) or a mixture of DMSO-D6 and deuterated chloroform ($CDCl_3$) at concentrations between 30-40 mg/mL using a Jeol spectrometer operating at 500 MHz (Jeol Ltd., Tokyo, Japan) for: (a) the hydrophobically-substituted polynucleophile (polymerization initiator) from which the polyglyceryl thickener is derived, i.e. $(Nu)_b$-Node-$(L'-Hphob)_h$ as described above; (b) polyglycerin-10 (Natrulon H-10 available from Lonza Group); and (c) the subject polyglyceryl thickener for which $DP_g$ is to be determined. Based on the reference spectra (a) and (b), the peaks associated with the five characteristic carbon-bonded (i.e. methylene/methine) protons of glyceryl units and the peaks associated with a selected number of characteristic protons of the Node-$(L'-Hphob)_h$ moiety are assigned. The area under the curve for peaks associated with the five glyceryl unit protons in spectrum (c) is calculated (minus any contribution from overlapping protons of Node-$(L'-Hphob)_h$) and divided by five to normalize for the corresponding number of protons per mole of glyceryl unit. The area under the curve for peaks associated with the selected characteristic protons of the Node-$(L'-Hphob)_h$ in spectrum (c) is calculated and divided by the total number of characteristic protons to normalize for the number of such protons per mole of Node-$(L'-Hphob)_h$. The $DP_g$ of the polyglyceryl thickener is then calculated as: [normalized area of polyglyceryl units]/[normalized area of Node-$(L'-Hphob)_h$]. The DPgs thus calculated are generally accurate to within ±5-10%

Figure 3:
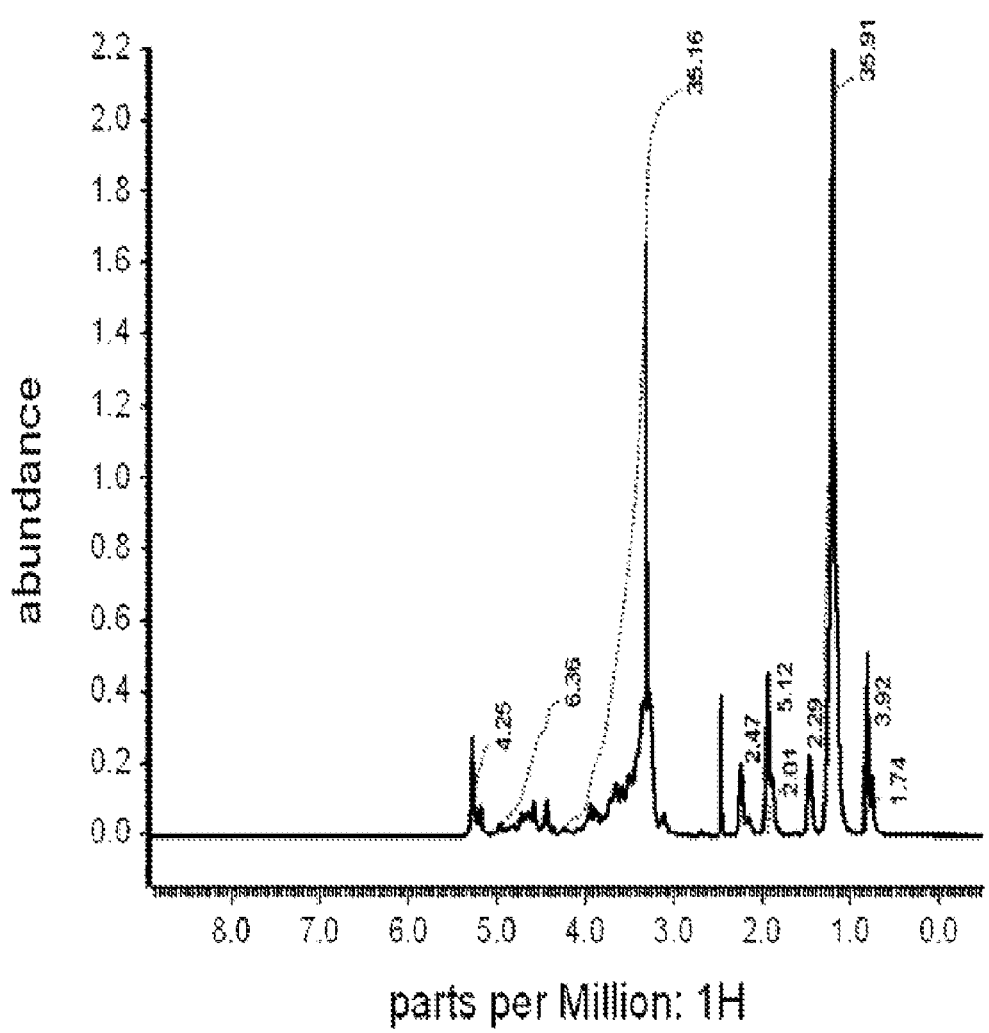
FIG. 3 is an $^1H$ NMR spectrum for a composition E1A as made in accord with the Examples.
Figure 4:
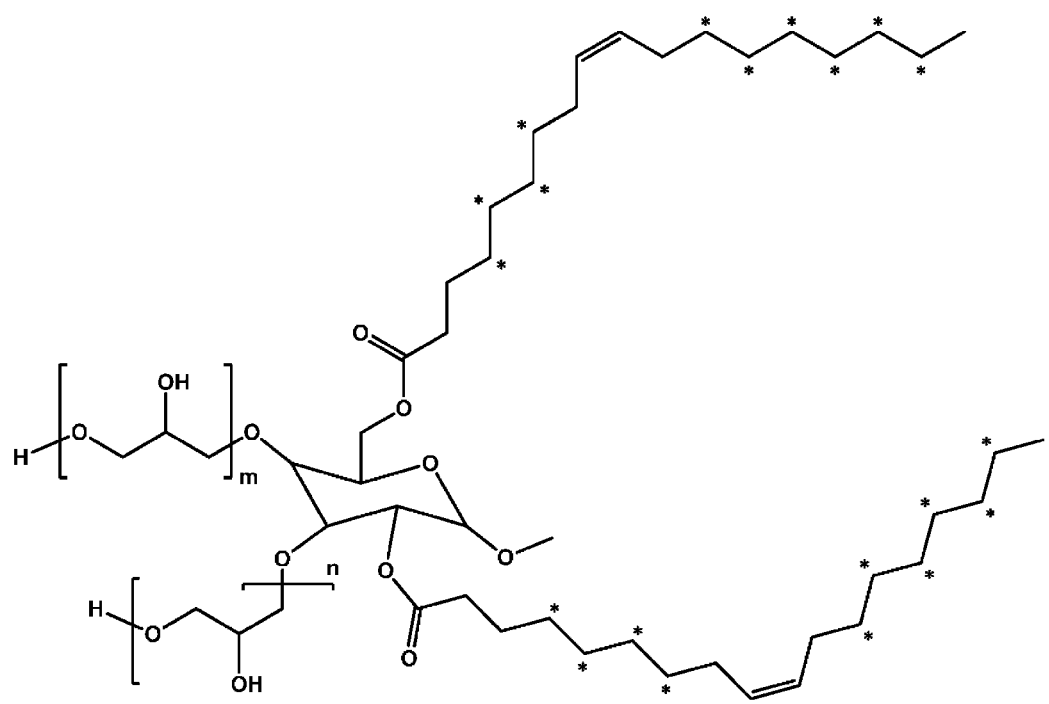
FIG. 4 is an illustration of 40 reference protons (indicated by a *) used as an internal reference to determine $DP_g$ for a composition E1A as made in accord with the Examples.

For the purpose of clarity the following example calculation is provided for a polyglyceryl thickener comprising polyglyceryl methyl glucose dioleate (E1A). $^1H$ NMR spectra were obtained as above for methyl glucose dioleate, polyglycerin-10 (Natrulon H-10 available from Lonza Group), and the polyglyceryl methyl glucose dioleate polyglyceryl thickener (E1A). Based on the reference spectra for methyl glucose dioleate and polyglycerin-10, the proton peaks between 3-4 ppm in the spectra for the polyglyceryl thickener were assigned to five protons of the polyglyceryl repeat units and five overlapping protons from the methyl glucose dioleate, and the proton peaks between 1-1.3 ppm were assigned to 40 characteristic protons on the methyl glucose dioleate hydrophobic groups (See, for example, FIGS. 3 and 4). The areas under the curve for the peaks were calculated and the $DP_g$ calculated using the following equation:

$$DP_g = \frac{\left[Area_{3-4ppm} - 5 \times \frac{Area_{1-1.3ppm}}{40}\right]}{5} \Big/ \frac{Area_{1-1.3ppm}}{40}$$

Hydrophilicity Index Test:

The following Hydrophilicity Index Test was performed on various polyglyceryl thickeners using an Antaris FT-NIR Analyzer (Thermo Fisher Scientific, Waltham, Mass.) equipped with transmission, fiber-optic and integrating sphere diffuse reflection modules. Real-time, on-line fiber optic measurements were conducted using small diameter (⅛") transmission probe (Axiom Analytical, Inc, Tustin, Calif.) immersed in the glassware reactor. Off-line measurements were conducted using integrated sphere module and the data analyzed using TQ Analyst software program provided by Thermo Fisher Scientific. The spectra from both, on-line and off-line measurements, were obtained using 64 scans with 4 $cm^{-1}$ resolution.

The Hydrophilicity Index (HI) test of the polyglyceryl thickener was conducted on series of NIR spectra obtained from off-line, room temperature measurements using the integrated sphere module. HI is a measure the relative proportions of hydrophilic (glyceryl units) vs. hydrophobic (hydrocarbon) character of the polyglyceryl thickeners produced. Using TQ Analyst software, the area under the —OH absorption band of glyceryl units (from 6,100 $cm^{-1}$ to 7500 $cm^{-1}$) was integrated and compared with the area integrated under the hydrophobic, hydrocarbon spectral area (5320 $cm^{-1}$ to 6050 $cm^{-1}$). The calculated ratio between hydrophilic and hydrophobic area is HI, and can be used to compare the hydrophilicity between the different samples. HI ratio is independent of the sample size/thickness and test temperature. Lower values of hydrophilicity index indicate less polyglycerol units have been incorporated. Similarly, a higher hydrophilicity index will indicate that more polyglycerol has been incorporated into the polyglyceryl thickener. In certain preferred embodiments HI is about 0.3 or greater. More preferred is HI of about 0.4 or greater. In certain embodiments, preferred HI is from about 0.4 to about 0.9, and more preferred is HI from about 0.5 to about 0.8.

Zero Shear Viscosity Test:

The following Zero Shear Viscosity Test was performed on various personal care compositions to determine the viscosity according to the present invention. Viscosities of test formulations were conducted at 25° C. using a controlled-stress rheometer (AR-2000, TA Instruments Ltd., New Castle, Del., USA). Steady-state shear stress sweeps were performed at 25.0±0.1° C. using a double-wall Couette geometry. Data acquisition and analysis were performed with the Rheology Advantage software v4.1.10 (TA Instruments Ltd., New Castle, Del., USA). Zero-shear apparent viscosities for samples that demonstrated Newtonian behavior are reported as the average of viscosity values obtained over a range of shear stresses (0.005-100 Pa). For pseudoplastic (shear-thinning) fluids, zero-shear apparent viscosities ($\eta_0$) were calculated via the fitting of shear stress sweep data to an Ellis viscosity model.

Formulation Foam Test:

The following Formulation Foam Test is performed on various cleansing compositions to determine the foam volume upon agitation according to the present invention. First, a solution of the test composition is prepared in simulated tap water. To represent the hardness of tap water, 0.36 g of calcium chloride is dissolved in 995 g of DI water. Five (5.0) grams of test composition is then added to this solution and mixed until homogeneous. To determine the Formulation Foam Volume, the test composition (1000 mL) was added to the sample tank of a SITA R-2000 foam tester (commercially available from Future Digital Scientific, Co.; Bethpage, N.Y.). The test parameters were set to repeat three runs (series count=3) of 250 ml sample size (fill volume=250 ml) with thirteen stir cycles (stir count=13) for a 15 second stir time per cycle (stir time=15 seconds) with the rotor spinning at 1200 RPM (revolution=1200) at a temperature setting of 30° C.±2° C. Foam volume data was collected at the end of each stir cycle and the average and standard deviation of the three runs was determined. The Maximum Foam Volume is reported as the value after the thirteenth stir cycle.

Example 1

Preparation of Polyglyceryl Thickeners (E1-E17)

Polyglyceryl thickener composition E1 was prepared as follows: to an appropriately-sized vessel fitted with $N_2$ sparge, reflux condenser, graduated addition funnel, and NIR reaction probe, 0.058 moles of methyl glucose dioleate (MGD), 0.050 moles of glyceryl carbonate and 0.0058 moles of $Ca(OCH_3)_2$ were added. The mixture was heated to about 80° C. and placed under vacuum to degas the mixture. The vacuum was broken and the mixture then heated slowly to 190° C. under $N_2$ sparge with appropriate agitation. After equilibrating at 190° C. for 30 min, GC (degassed, 1.15 moles) was slowly added to the reactor over 2.5 hr. After completion of the addition, the reaction mixture was stirred at 190° C. until all of the glycerol carbonate was consumed. All degassing steps (moisture level measurements), reaction progress and GC consumption were monitored in situ via real-time NIR analysis. After the reaction was complete the material was cooled and discharged to an appropriate container.

Additional polyglyceryl thickeners, E2-E17 were synthesized by varying the type or proportions of starting materials: polymerization initiator, glyceryl monomer, and/or base catalyst. The variation in starting materials used, reaction conditions, and products are summarized in the Table 1 below. For E9-E11, and E13 AGC, synthesized in accord with the procedure below, and GC were added sequentially to the reaction mixture, whereas for E14, AGC and GC were added simultaneously. Additionally, the time of addition, total reaction time and temperature of the various reactions, as well as the resulting phases are shown in Table 2 below. The following abbreviations are used therein: MGD=methyl glucose dioleate, SO=sorbitan oleate, SSO=sorbitan sesquioleate, GC=glyceryl carbonate, AGC/GC=combination of acetylated glyceryl carbonate and glyceryl carbonate, SDO=sorbitan dioleate.

Preparation of Acetyl Glyceryl Carbonate (AGC): the Following is a General Lab-Scale procedure for the preparation of AGC: to a clean, dry 250 mL two-neck flask equipped with a magnetic stirrer, near IR probe, and a condenser, was added glycerol carbonate (82.6 g, 0.70 mol), acetic anhydride (70.0 g, 0.68 mol), and two drops of pyridine. In the first stage of the reaction, the contents were heated under reflux for six hours at 100° C. Conversion of glyceryl carbonate to AcGC was monitored via FT-NIR by following disappearance of the characteristic —OH (hydroxyl) absorption band for glyceryl carbonate at 7000 $cm^{-1}$. In the second stage of the reaction, the acetic acid byproduct was removed via distillation at 45° C. under reduced pressure (ultimate vacuum=3.5 Torr). Removal of acetic acid was monitored via near IR by following the disappearance of the acetic acid peak at 6850 $cm^{-1}$. The resulting AcGC was stored under nitrogen blanket until use.

TABLE 1

Synthesis of E1-E17

| Ex. # | Polymerization Initiator type | moles | Glyceryl monomer type | moles | Base catalyst type | moles |
|---|---|---|---|---|---|---|
| E1 | MGD | 0.0575 | GC | 1.1499 | $Ca(OCH_3)_2$ | 0.0058 |
| E2 | MGD | 0.0575 | GC | 1.2740 | $Ca(OCH_3)_2$ | 0.0058 |
| E3 | MGD | 0.0575 | GC | 1.1499 | $KOCH_3$ | 0.0116 |
| E4 | MGD | 0.0575 | GC | 0.8413 | $K_2CO_3$ | 0.0058 |
| E5 | MGD | 0.0575 | GC | 1.1300 | KGC (20%) | 0.0028 |
| E6 | MGD | 0.0575 | GC | 1.1525 | $K_2CO_3$ | 0.0057 |
| E7 | MGD | 0.0575 | GC | 1.1499 | $KOC(CH_3)_3$ | 0.0058 |
| E8 | MGD | 0.0575 | GC | 1.1240 | KGC (10%) | 0.0029 |
| E9 | MGD | 0.0349 | AGC/GC (seq) | 0.7150/ 1.1431 | $KOCH_3$ | 0.0035 |
| E10 | MGD | 0.0575 | AGC/GC (seq) | 0.0440/ 1.149 | $KOCH_3$ | 0.0035 |
| E11 | MGD | 0.0575 | AGC/GC (seq) | 0.1300/ 0.5655 | $KOCH_3$ | 0.0035 |
| E12 | MGD | 0.0575 | GC | 0.5710 | $Ca(OCH_3)_2$ | 0.0058 |
| E13 | MGD | 0.0575 | AGC/GC (seq) | 0.187/ 0.571 | $KOCH_3$ | 0.0035 |
| E14 | MGD | 0.0575 | AGC/GC (random) | 0.187/ 0.571 | $KOCH_3$ | 0.0035 |
| E15 | SO | 0.0575 | GC | 1.1499 | $Ca(OCH_3)_2$ | 0.0057 |
| E16 | SSO | 0.0575 | GC | 1.1499 | $Ca(OCH_3)_2$ | 0.0057 |
| E17 | SDO | 0.0575 | GC | 1.1499 | $Ca(OCH_3)_2$ | 0.0057 |

TABLE 2

Reaction Conditions and Phase Nature of E1-E17

| Ex. # | time add. (hrs) | Total reaction time (hrs) | Temperature (° C.) | Product |
|---|---|---|---|---|
| E1 | 2.5 | 4.30 | 190 | two-phase |
| E2 | 2.5 | 5.53 | 190 | two-phase |
| E3 | 3.17 | 4.17 | 190-200 | two-phase |
| E4 | 6.00 | 6.00 | 190-200 | two-phase |
| E5 | 5.50 | 7.00 | 190 | two-phase |
| E6 | 9.50 | 10.00 | 190-200 | two-phase |
| E7 | 7.80 | 8.17 | 190 | two-phase |
| E8 | 3.75 | 5.00 | 180 | two-phase |
| E9 | 1.75 | 10.95 | 175 | one-phase |
| E10 | 2.50 | 4.75 | 180 | two-phase |
| E11 | 3.46 | 6.30 | 180 | two-phase |
| E12 | 2.43 | 3.51 | 190 | two-phase |
| E13 | 5.25 | 6.25 | 180 | two-phase |
| E14 | 3.83 | 4.83 | 180 | one-phase |
| E15 | 2.75 | 5.00 | 190 | two-phase |
| E16 | 2.66 | 4.66 | 190 | two-phase |
| E17 | 3.17 | 5.17 | 190 | two-phase |

The results above indicate that in nearly all cases (except E9 and E14), the reaction product included two-phases. It was observed that the top phase was less viscous and lighter in color than the bottom phase.

Example 2

Properties of Polyglyceryl Thickeners

Examples E1-E17 were characterized for Average Degree of Glyceryl Polymerization and Hydrophilicity Index in accord with the respective Procedure and Test above. For those reaction products that included two phases, the phases were separated from one another by decanting off the top layer. The top phase/layer was identified as "A" and the bottom phase was identified as "B." For example, the top phase of Inventive Example, E1 is identified as Inventive Example E1A, whereas the bottom phase of Inventive Example E1 is identified as Example E1B. Average Degree of Glyceryl Polymerization and Hydrophilicity Index for the resulting compositions are reported in Table 3 below.

TABLE 3

Properties of Inventive Polyglyceryl Thickeners

| EX. # | Glyceryl DP | Hydrophilicity Index |
|---|---|---|
| E1A | 6.3 | 0.60 |
| E1B | 29.9 | 1.47 |
| E2A | 7.0 | 0.66 |
| E2B | 28.6 | 1.52 |
| E3A | 7.6 | 0.65 |
| E3B | 12.1 | 1.82 |
| E4A | 3.6 | 0.43 |
| E5A | 6.1 | 0.51 |
| E5B | 79.7 | 2.22 |
| E8A | 4.0 | 0.48 |
| E9 | 61.0 | 1.59 |
| E10A | 3.9 | 0.52 |
| E10B | 87.0 | 2.38 |
| E11A | 4.8 | 0.62 |
| E12A | 5.1 | 0.52 |
| E12B | 38.8 | 1.16 |
| E13A | 6.8 | 0.63 |
| E13B | 17.0 | 1.61 |
| E14 | 9.9 | 0.71 |
| E15A | 24.6 | 1.15 |
| E15B | 47.6 | 1.82 |
| E16A | 27.0 | 1.11 |
| E16B | 38.6 | 1.69 |
| E17A | 6.3 | 0.66 |
| E17B | 37.9 | 1.72 |

From the results above, it appears that the top phases tended to have a low $DP_g$ while the bottom phases tended to have a high $DP_g$. As expected, and apparent from the data, $DP_g$ correlates well with hydrophilicity index.

Also notable is the effect of degree of hydrophobic substitution. Inventive Examples E1-E14 used methyl glucose dioleate, which nominally has an average degree of substitution of hydrophobic moieties of 2.0, and therefore the nominal average number of hydrophobic groups per primary linking group in these particular polyglyceryl thickeners is 2.0/4=0.5. Inventive Example E15 uses sorbitan oleate, which nominally has an average degree of substitution of hydrophobic moieties of 1.0, and therefore the nominal average number of hydrophobic groups per primary linking group in this particular polyglyceryl thickener is 1.0/4=0.25. Inventive Example E16 uses sorbitan sesquioleate, which nominally has an average degree of substitution of hydrophobic moieties of 1.5 and therefore the nominal average number of hydrophobic groups per primary linking group in this particular polyglyceryl thickener is 1.5/4=0.375). Inventive Examples E15(A,B) and E16(A,B), which had less hydrophobic substitution, tended to produce relatively high $DP_g$ polyglyceryls, whereas the other Inventive Examples were more readily capable of producing a broader range of $DP_g$.

Example 3

Preparation of Comparative Examples ($C_1$-$C_8$) and Examples (E18 to E42)

Liquid cleanser formulations were prepared as follows: to a beaker fitted with a mechanical stirrer and hotplate, water, ammonium lauryl sulfate, and ammonium laureth sulfate were added. This was mixed at low-medium speed and heat was slowly applied to the batch to increase the temperature to 75° C. When the batch reached 75° C., cocamide MEA and a particular commercially-available thickener/test material was added. Heating was stopped after the ingredients were completely dissolved and the batch was allowed to cool to approx. 25° C., while mixing was continued at medium speed. When the batch reached 25° C., sodium chloride and DMDM hydantoin were added and mix until completely dissolved. pH was adjusted to 6.4±0.2 using citric acid or sodium hydroxide solution. Water was added in q.s. to 100%. The composition of the various comparative compositions (and weight percentages of ingredients) are shown in the Table 4 below.

TABLE 4

Comparative Personal Care Compositions

| Thickening or Test Material/ Tradename/ | Ingredient/INCI Name | C1 | C2 | C3 | C4 | C5 | C6 | C7 | C8 |
|---|---|---|---|---|---|---|---|---|---|
| Control (Unthickened) | Control (Unthickened) | — | — | — | — | — | — | — | — |
| Natrulon H-10 | Polyglycerin-10 | — | 5.00 | — | — | — | — | — | — |
| Glucate DO | Methyl Glucose Dioleate | — | — | 5.00 | — | — | — | — | — |
| Glucamate DOE-120 | PEG-120 Methyl Glucose Dioleate | — | — | — | 5.00 | — | — | — | — |
| Tego Care 450 | Polyglyceryl-3 Methyl Glucose Distearate | — | — | — | — | 5.00 | — | — | — |
| SPAN 80-NV-IQ-(AP | Sorbitan Oleate | — | — | — | — | — | 5.00 | — | — |
| SPAN 83-NV-LQ-(AP) | Sorbitan Sesquioleate | — | — | — | — | — | — | 5.00 | — |
| Sorbitan Dioleate | Sorbitan Dioleate | — | — | — | — | — | — | — | 5.00 |
| Standapol A (28%) | Ammonium Lauryl Sulfate | 10.92 | 10.92 | 10.92 | 10.92 | 10.92 | 10.92 | 10.92 | 10.92 |
| Standapol EA-2 (25%) | Ammonium Laureth Sulfate | 4.39 | 4.39 | 4.39 | 4.39 | 4.39 | 4.39 | 4.39 | 4.39 |
| Comperlan 100 (95%) | Cocamide MEA | 1.24 | 1.24 | 1.24 | 1.24 | 1.24 | 1.24 | 1.24 | 1.24 |
| Sodium Chloride | Sodium Chloride | 0.40 | 0.40 | 0.40 | 0.40 | 0.40 | 0.40 | 0.40 | 0.40 |
| Glydant | DMDM Hydantoin | 0.06 | 0.06 | 0.06 | 0.06 | 0.06 | 0.06 | 0.06 | 0.06 |

TABLE 4-continued

Comparative Personal Care Compositions

| Thickening or Test Material/ Tradename/ | Ingredient/INCI Name | C1 | C2 | C3 | C4 | C5 | C6 | C7 | C8 |
|---|---|---|---|---|---|---|---|---|---|
| Sodium Hydroxide solution (20%) | Sodium Hydroxide | q.s. | q.s. | q.s. | q.s. | q.s. | q.s. | q.s. | q.s. |
| Citric Acid solution (20%) | Citric Acid | q.s. | q.s. | q.s. | q.s. | q.s. | q.s. | q.s. | q.s. |
| Purified Water | Water | q.s. | q.s. | q.s. | q.s. | q.s. | q.s. | q.s. | q.s. |

NATRULON H-10 is available from Lonza Group of Allendale, NJ. GLUCATE DO and GLUCAMATE DOE-120 are available from Lubrizol of Wickliffe, OH. TEGO CARE 450 is available from Evonik Goldschmidt GmbH of Essen, Germany. SPAN 80 and 83 are available from Croda of Edison, NJ. STANDAPOL and COMPERLAN are available from Cognis Corp. (now BASF) of Ambler, PA.

Inventive personal care compositions were also prepared in a similar manner to the comparative personal care compositions of Table 4, except that particular polyglyceryl thickeners of Example I were used. The compositions of the various formulations (and weight percentages of ingredients) are shown in the Table 5 (E18-E26), Table 6 (E27-E35), and Table 7 (Examples E36-E42), below.

TABLE 5

Personal Care Compositions with Polyglyceryl Thickeners

| Thickening Material/ Tradename/ Example Number | Ingredient/INCI Name | E18 | E19 | E20 | E21 | E22 | E23 | E24 | E25 | E26 |
|---|---|---|---|---|---|---|---|---|---|---|
| E1A | PGMGD | 5.00 | — | — | — | — | — | — | — | — |
| E1B | PGMGD | — | 5.00 | — | — | — | — | — | — | — |
| E2A | PGMGD | — | — | 5.00 | — | — | — | — | — | — |
| E2B | PGMGD | — | — | — | 5.00 | — | — | — | — | — |
| E3A | PGMGD | — | — | — | — | 5.00 | — | — | — | — |
| E3B | PGMGD | — | — | — | — | — | 5.00 | — | — | — |
| E4A | PGMGD | — | — | — | — | — | — | 5.00 | — | — |
| E5A | PGMGD | — | — | — | — | — | — | — | 5.00 | — |
| E5B | PGMGD | — | — | — | — | — | — | — | — | 5.00 |
| Standapol A (28%) | Ammonium Lauryl Sulfate | 10.92 | 10.92 | 10.92 | 10.92 | 10.92 | 10.92 | 10.92 | 10.92 | 10.92 |
| Standapol EA-2 (25%) | Ammonium Laureth Sulfate | 4.39 | 4.39 | 4.39 | 4.39 | 4.39 | 4.39 | 4.39 | 4.39 | 4.39 |
| Comperlan 100 (95%) | Cocamide MEA | 1.24 | 1.24 | 1.24 | 1.24 | 1.24 | 1.24 | 1.24 | 1.24 | 1.24 |
| Sodium Chloride | Sodium Chloride | 0.40 | 0.40 | 0.40 | 0.40 | 0.40 | 0.40 | 0.40 | 0.40 | 0.40 |
| Glydant | DMDM Hydantoin | 0.06 | 0.06 | 0.06 | 0.06 | 0.06 | 0.06 | 0.06 | 0.06 | 0.06 |
| Sodium Hydroxide solution (20%) | Sodium Hydroxide | q.s. | q.s. | q.s. | q.s. | q.s. | q.s. | q.s. | q.s. | q.s. |
| Citric Acid solution (20%) | Citric Acid | q.s. | q.s. | q.s. | q.s. | q.s. | q.s. | q.s. | q.s. | q.s. |
| Purified Water | Water | q.s. | q.s. | q.s. | q.s. | q.s. | q.s. | q.s. | q.s. | q.s. |

TABLE 6

Personal Care Compositions with Polyglyceryl Thickeners

| Thickening Material/ Tradename/ Example Number | Ingredient/INCI Name | E27 | E28 | E29 | E30 | E31 | E32 | E33 | E34 | E35 |
|---|---|---|---|---|---|---|---|---|---|---|
| E8A | PGMGD | 5.00 | — | — | — | — | — | — | — | — |
| E9 | AGC/PG MGD | — | 5.00 | — | — | — | — | — | — | — |
| E10A | AGC/PG MGD | — | — | 5.00 | — | — | — | — | — | — |
| E10B | AGC/PG MGD | — | — | — | 5.00 | — | — | — | — | — |
| E11A | AGC/PG MGD | — | — | — | — | 5.00 | — | — | — | — |
| E12A | PGMGD | — | — | — | — | — | 5.00 | — | — | — |
| E12B | PGMGD | — | — | — | — | — | — | 5.00 | — | — |
| E13A | AGC/PG MGD | — | — | — | — | — | — | — | 5.00 | — |
| E13B | AGC/PG MGD | — | — | — | — | — | — | — | — | 5.00 |
| Standapol A (28%) | Ammonium Lauryl Sulfate | 10.92 | 10.92 | 10.92 | 10.92 | 10.92 | 10.92 | 10.92 | 10.92 | 10.92 |

TABLE 6-continued

Personal Care Compositions with Polyglyceryl Thickeners

| Thickening Material/ Tradename/ Example Number | Ingredient/INCI Name | E27 | E28 | E29 | E30 | E31 | E32 | E33 | E34 | E35 |
|---|---|---|---|---|---|---|---|---|---|---|
| Standapol EA-2 (25%) | Ammonium Laureth Sulfate | 4.39 | 4.39 | 4.39 | 4.39 | 4.39 | 4.39 | 4.39 | 4.39 | 4.39 |
| Comperlan 100 (95%) | Cocamide MEA | 1.24 | 1.24 | 1.24 | 1.24 | 1.24 | 1.24 | 1.24 | 1.24 | 1.24 |
| Sodium Chloride | Sodium Chloride | 0.40 | 0.40 | 0.40 | 0.40 | 0.40 | 0.40 | 0.40 | 0.40 | 0.40 |
| Glydant | DMDM Hydantoin | 0.06 | 0.06 | 0.06 | 0.06 | 0.06 | 0.06 | 0.06 | 0.06 | 0.06 |
| Sodium Hydroxide solution (20%) | Sodium Hydroxide | q.s. | q.s. | q.s. | q.s. | q.s. | q.s. | q.s. | q.s. | q.s. |
| Citric Acid solution (20%) | Citric Acid | q.s. | q.s. | q.s. | q.s. | q.s. | q.s. | q.s. | q.s. | q.s. |
| Purified Water | Water | q.s. | q.s. | q.s. | q.s. | q.s. | q.s. | q.s. | q.s. | q.s. |

TABLE 7

Personal Care Compositions with Polyglyceryl Thickeners

| Thickening Material/ Tradename/ Example Number | Ingredient/INCI Name | E36 | E37 | E38 | E39 | E40 | E41 | E42 |
|---|---|---|---|---|---|---|---|---|
| E14 | AGC/PG MGD (Rand) | 5.00 | — | — | — | — | — | — |
| E15A | PGSO | — | 5.00 | — | — | — | — | — |
| E15B | PGSO | — | — | 5.00 | — | — | — | — |
| E16A | PGSSO | — | — | — | 5.00 | — | — | — |
| E16B | PGSSO | — | — | — | — | 5.00 | — | — |
| E17A | PGSDO | — | — | — | — | — | 5.00 | — |
| E17B | PGSDO | — | — | — | — | — | — | 5.00 |
| Standapol A (28%) | Ammonium Lauryl Sulfate | 10.92 | 10.92 | 10.92 | 10.92 | 10.92 | 10.92 | 10.92 |
| Standapol EA-2 (25%) | Ammonium Laureth Sulfate | 4.39 | 4.39 | 4.39 | 4.39 | 4.39 | 4.39 | 4.39 |
| Comperlan 100 (95%) | Cocamide MEA | 1.24 | 1.24 | 1.24 | 1.24 | 1.24 | 1.24 | 1.24 |
| Sodium Chloride | Sodium Chloride | 0.40 | 0.40 | 0.40 | 0.40 | 0.40 | 0.40 | 0.40 |
| Glydant | DMDM Hydantoin | 0.06 | 0.06 | 0.06 | 0.06 | 0.06 | 0.06 | 0.06 |
| Sodium Hydroxide solution (20%) | Sodium Hydroxide | q.s. | q.s. | q.s. | q.s. | q.s. | q.s. | q.s. |
| Citric Acid solution (20%) | Citric Acid | q.s. | q.s. | q.s. | q.s. | q.s. | q.s. | q.s. |
| Purified Water | Water | q.s. | q.s. | q.s. | q.s. | q.s. | q.s. | q.s. |

Example 4

Rheology of Compositions and Comparative Examples

The rheology of comparative Examples $C_1$-$C_8$ and Examples E18-E42 was analyzed according to the Zero Shear Viscosity Test to determine the thickening efficiency of the test material/thickener. The results of these tests are shown Table 8, below.

TABLE 8

Rheology and Appearance of Personal Care Compositions

| Example | $\eta_0$(cP) | Rheology Type | Appearance (qualitative) |
|---|---|---|---|
| C1 | 941 | Newtonian | clear (no color) |
| C2 | 79 | Newtonian | clear (no color) |
| C3 | — | — | opaque (no color) - unstable |
| C4 | 575 | Newtonian | clear (no color) |
| C5 | 20,450 | Newtonian | opaque (no color) - unstable over time |
| C6 | — | Newtonian | opaque (no color) - unstable |
| C7 | — | Newtonian | opaque (no color) - unstable |
| C8 | — | Newtonian | opaque (no color) - unstable |
| E18 | 6600 | Newtonian | clear (light amber color) |
| E19 | 43 | Newtonian | clear (amber color) |
| E20 | 9671 | Newtonian | hazy (light straw color) |
| E21 | 1193 | Newtonian | hazy (light amber color) |
| E22 | 8067 | Newtonian | hazy (light straw color) |
| E23 | 3000 | Newtonian | hazy (light amber color) |
| E24 | 2777 | Newtonian | opaque (light straw color) |
| E25 | 2788 | Newtonian | hazy (light straw color) |
| E26 | 43 | Newtonian | opaque (light straw color) |
| E27 | 2948 | Newtonian | opaque (straw color) |
| E28 | 16 | Newtonian | clear (amber color) |
| E29 | 3841 | Newtonian | opaque (light straw color) |
| E30 | 21 | Newtonian | clear (light straw color) |
| E31 | 4678 | Newtonian | hazy (light straw color) |
| E32 | 3517 | Newtonian | opaque (straw color) |
| E33 | 170 | Newtonian | hazy (straw color) |

TABLE 8-continued

Rheology and Appearance of Personal Care Compositions

| Example | η₀(cP) | Rheology Type | Appearance (qualitative) |
|---|---|---|---|
| E34 | 6657 | Newtonian | clear (light straw color) |
| E35 | 66 | Newtonian | clear (light straw color) |
| E36 | 905 | Newtonian | clear (light straw color) |
| E37 | 326 | Newtonian | slight haze (light straw color) |
| E38 | 92 | Newtonian | clear (light straw color) w/small precipitate |
| E39 | 476 | Newtonian | slight haze (light straw color) |
| E40 | 159 | Newtonian | clear (light straw color) w/small precipitate |
| E41 | 2274 | Newtonian | hazy (light straw color) |
| E42 | 229 | Newtonian | hazy (light straw color) |

As can be seen in Table 8, the comparative examples showed no ability to thicken the base "control" formulation (Comparative Example C1). The only comparative example which showed some apparent initial ability to thicken was Comparative Example C5, which used Polyglyceryl-3 Methyl Glucose Distearate (believed to be a polyglyceryl emulsifier with a $DP_g$ of 3, a methyl glucose residue node structure). However, Comparative Example C5 was not stable and phase separated when standing at room temperature overnight. By comparison the tested Examples of the present invention have show stability while standing at room temperature for at least several months, to a year, or more.

Furthermore, to show the effect of $DP_g$, FIG. 1 shows Zero Shear Viscosity plotted vs. $DP_g$ for Inventive Examples E18 to E42. It is clear from the Figure that those polyglyceryl thickeners with a DP greater than 3 and less than about 11 built viscosity effectively, whereas those with a higher $DP_g$ tend not to.

Also notable is the effect of average degree of substitution with hydrophobic moieties. Examples E37-E40, which as discussed above in Example 2, used a polyglyceryl compound with an average degree of substitution of hydrophobic moieties of 1.0 or 1.5 (an average number of hydrophobic groups per primary linking group of either 0.25 or 0.375 respectively) did not build viscosity.

Example 5

Dose-Response Rheology of Compositions Comprising Polyglyceryl Thickeners

The following personal care compositions, Examples E43-56 were prepared. These compositions were tested for Zero Shear Viscosity to evaluate the effect of polyglyceryl thickener concentration on viscosity. Examples E1A, E13A, E14, E15A, E16A, and E17A as well as Example E1B were tested in a formulation base that was identical to the base of Example 2. The concentrations and particular polyglyceryl thickeners are listed in Tables 9a-c, below:

TABLE 9a

| Thickening Material/ Tradename/ Example Number | Ingredient Name | E18 | E43 | E44 | E19 | E45 | E46 | E34 | E47 | E48 |
|---|---|---|---|---|---|---|---|---|---|---|
| E1A | PGMGD | 5.00 | — | — | — | — | — | — | — | — |
| E1A | PGMGD | — | 3.00 | — | — | — | — | — | — | — |
| E1A | PGMGD | — | — | 1.00 | — | — | — | — | — | — |
| E1B | PGMGD | — | — | — | 5.00 | — | — | — | — | — |
| E1B | PGMGD | — | — | — | — | 3.00 | — | — | — | — |
| E1B | PGMGD | — | — | — | — | — | 1.00 | — | — | — |
| E13A | AGC/PG MGD | — | — | — | — | — | — | 5.00 | — | — |
| E13A | AGC/PG MGD | — | — | — | — | — | — | — | 3.00 | — |
| E13A | AGC/PG MGD | — | — | — | — | — | — | — | — | 1.00 |

TABLE 9b

| Thickening Material/ Tradename/ Example Number | Ingredient Name | E36 | E49 | E50 | E37 | E51 | E52 | E39 | E53 | E54 |
|---|---|---|---|---|---|---|---|---|---|---|
| E14 | AGC/PG MGD (Rand) | 5.00 | — | — | — | — | — | — | — | — |
| E14 | AGC/PG MGD (Rand) | — | 3.00 | — | — | — | — | — | — | — |
| E14 | AGC/PG MGD (Rand) | — | — | 1.00 | — | — | — | — | — | — |
| E15A | PGSO | — | — | — | 5.00 | — | — | — | — | — |
| E15A | PGSO | — | — | — | — | 3.00 | — | — | — | — |
| E15A | PGSO | — | — | — | — | — | 1.00 | — | — | — |
| E16A | PGSSO | — | — | — | — | — | — | 5.00 | — | — |
| E16A | PGSSO | — | — | — | — | — | — | — | 3.00 | — |
| E16A | PGSSO | — | — | — | — | — | — | — | — | 1.00 |

TABLE 9c

| Thickening Material/ Tradename/ Example Number | Ingredient Name | E41 | E55 | E56 |
|---|---|---|---|---|
| E17A | PGSDO | 5.00 | — | — |
| E17A | PGSDO | — | 3.00 | — |
| E17A | PGSDO | — | — | 1.00 |

Figure 2:
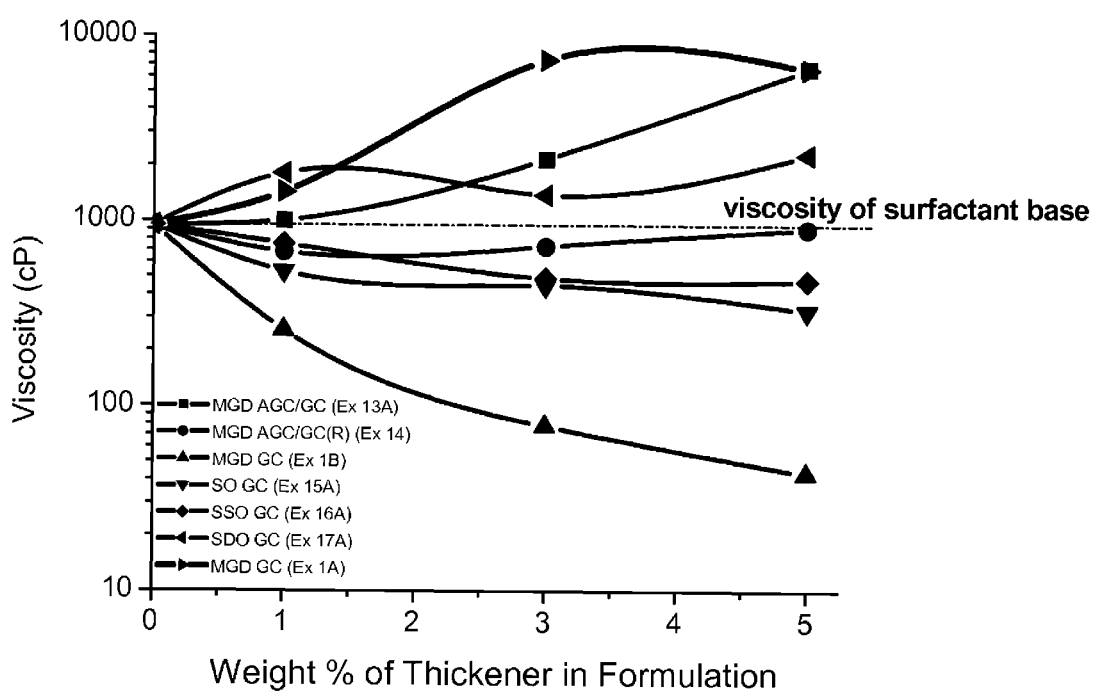
FIG. 2 is a graphical depiction of the relative viscosity compared to base as a function of wt % of polyglyceryl thickener in a formulation measured for certain compositions of the claimed invention.

The results are shown in FIG. 2. As can be seen from the figure, when thickener concentration is increased over the range from 1 to 5 wt % compositions comprising (MGD w/GC) Sample 1A showed an increase of 487-5659 cP (over the viscosity of the base), compositions comprising (MGD w/GC and AGC) Sample 13A ($DP_g$ of 6.8) showed an increase of 57-5716 cP, and compositions comprising (SDO w/GC) Sample 17A ($DP_g$ of 6.3) showed an increase of 860-1333 cP. Compositions comprising the polyglyceryl thickener of Example E14, which has a $DP_g$ of 9.9 (Examples E36, 49 and 50) shows some "upward sloping" behavior of viscosity versus thickener concentration.

However, compositions comprising the polyglyceryl compound of Example E16A, which has a $DP_g$ of 27.0 and an average of 1.5 oleate hydrophobes, compositions with the polyglyceryl compound of Example E15A, which has a $DP_g$ of 24.6 and a single oleate hydrophobe, and compositions with the polyglyceryl compound of Example E1B which has a $DP_g$ of 29.9 and two oleate hydrophobes, showed reduced viscosity versus the control which continued to decrease as the concentration of polyglyceryl compound was increased.

What is claimed is:

1. A polyglyceryl composition comprising one or more compounds characterized by the following structure:
   a node structure that is a polynucleophile remnant derived from methyl glucoside or sorbitan;
   one or more (poly)glyceryl groups; and
   one or more hydrophobic moieties;
   wherein each of said one or more (poly)glyceryl groups is linked to said node structure by a first primary linking group, said one or more hydrophobic moieties are each independently linked either to said node structure by a primary linking group or to one of said (poly)glyceryl groups by a secondary linking group;
   and wherein said polyglyceryl thickener composition has an average degree of glyceryl polymerization of from greater than 3 to less than about 11 and an average number of hydrophobic groups per primary linking group of about 0.35 or greater; provided that if the node structure is a polynucleophile remnant derived from sorbitan then said one or more compounds comprises a polyglyceryl sorbitan diester compound having from greater than 3 to about 11 glyceryl groups.

2. The composition of claim 1 wherein each primary and secondary linking group is independently selected from: —O—, —C(O)O—, —N(R)$_2$—, or —N(R)C(O)—, where each R is independently H or methyl.

3. The composition of claim 1 wherein each of said one or more hydrophobic moieties contains a carbon-carbon chain of at least six carbons in which none of the six carbons is a carbonyl carbon or has a hydrophilic moiety bonded directly to the at least six carbons.

4. The composition of claim 1 wherein said composition has from about 0.35 average hydrophobic moieties per primary linking group to about 0.55 average hydrophobic moieties per primary linking group.

5. The composition of claim 1 wherein the composition has an average degree of hydrophobic substitution of about 1.5 or more hydrophobic moieties per molecule.

6. The composition of claim 1 wherein the composition has an average degree of hydrophobic substitution of about 1.5 to about 2.2 hydrophobic moieties per molecule.

7. The composition of claim 1 wherein said one or more compounds are further characterized by the Formula I:

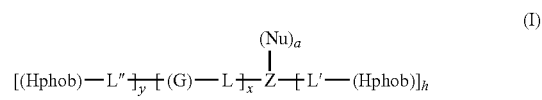

wherein:

Z is a polynucleophile remnant derived from methyl glucoside or sorbitan;

each G is an independently selected (poly)glyceryl group;

each (Hphob) is an independently selected hydrophobic moiety;

each L is an independently selected primary linking group;

each L' is an independently selected primary linking group;

each L" is an independently selected secondary linking group;

each (Nu) is an independently selected nucleophilic group;

x is from 1 to 4;

h is from 0 to 3;

y is from 0 to 4;

a is from 0 to 3;

the sum of x+h+a is 4; and the sum of h+y is from 1 to 4.

8. The composition of claim 7 wherein Z is a moiety of the structure:

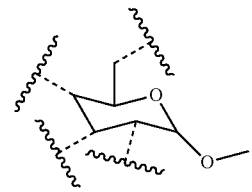

9. The composition of claim 7 wherein Z is a moiety of the structure:

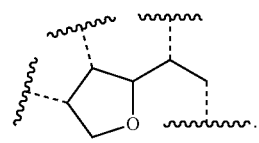

10. The composition of claim 7 wherein at least one of said one or more compounds is a polyglyceryl methyl glucose dioleate compound of the formula:

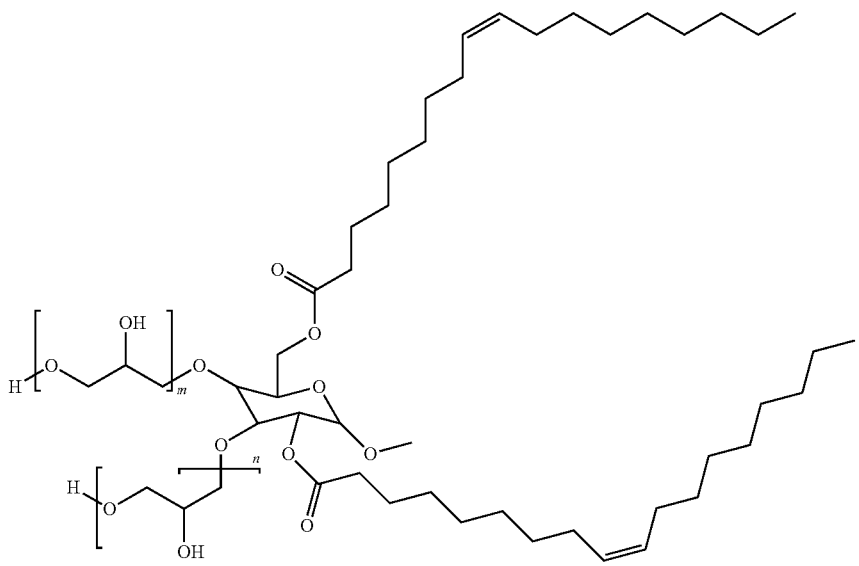

wherein m+n is from greater than 3 to about 11.

11. The composition of claim 10 wherein said composition comprises greater than 50 mol % of said polyglyceryl methyl glucose dioleate compounds.

12. The composition of claim 7 wherein at least one of said one or more compounds is a polyglyceryl sorbitan dioleate compound of the formula:

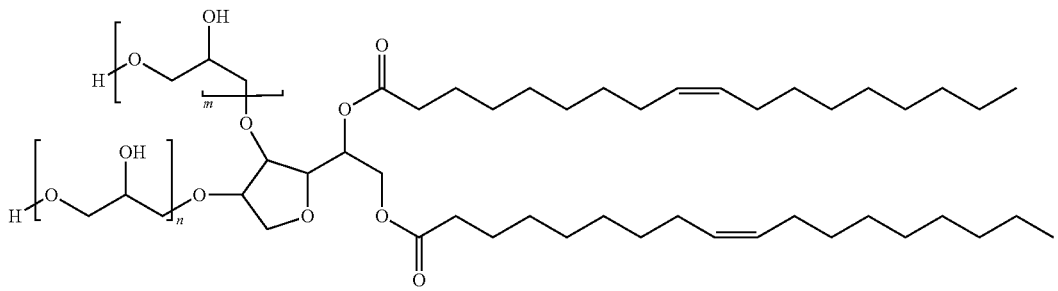

wherein m+n is from greater than 3 to about 11.

13. The composition of claim 12 wherein said composition comprises greater than 50 mol % of said polyglyceryl sorbitan dioleate compounds.

14. A polyglyceryl composition comprising one or more compounds characterized by the following structure:

a structure that is a polynucleophile remnant derived from methyl glucoside or sorbitan;

one or more (poly)glyceryl groups; and one or more hydrophobic moieties;

wherein each of said one or more (poly)glyceryl groups is linked to said node structure by a first primary linking group, said one or more hydrophobic moieties are each independently linked either to said node structure by a primary linking group or to one of said (poly)glyceryl groups by a secondary linking group;

and wherein said polyglyceryl thickener composition has a hydrophilicity index of from greater than 0.4 to less than about 0.9 and an average number of hydrophobic groups per primary linking group of about 0.35 or greater, provided that if the node structure is a polynucleophile remnant derived from sorbitan then said one or more compounds comprises a polyglyceryl sorbitan diester compound having from greater than 3 to about 11 glyceryl groups.

15. The composition of claim 14 wherein said node structure is a polynucleophile remnant derived from methyl glucoside.

16. The composition of claim 14 wherein each primary and secondary linking group is independently selected from: —O—, —C(O)O—, —N(R)$_2$—, or —N(R)C(O)—, where each R is independently H or methyl.

17. The composition of claim 14 wherein said composition has from about 0.35 average hydrophobic moieties per primary linking group to about 0.55 average hydrophobic moieties per primary linking group.

18. The composition of claim 14 wherein said one or more compounds are further characterized by the Formula I:

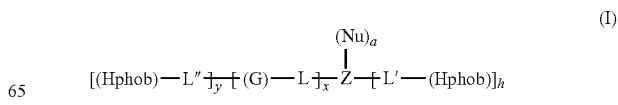

wherein:
Z is a polynucleophile remnant derived from methyl glucoside or sorbitan;
each G is an independently selected (poly)glyceryl group;
each (Hphob) is an independently selected hydrophobic moiety;
each L is an independently selected primary linking group;
each L' is an independently selected primary linking group;
each L" is an independently selected secondary linking group;

each (Nu) is an independently selected nucleophilic group;
x is from 1 to 4;
h is from 0 to 3;
y is from 0 to 4;
a is from 0 to 3;
the sum of x+h+a is 4; and
the sum of h+y is from 1 to 4.

19. The composition of claim 18 wherein at least one of said one or more compounds is a polyglyceryl methyl glucose dioleate compound of the formula:

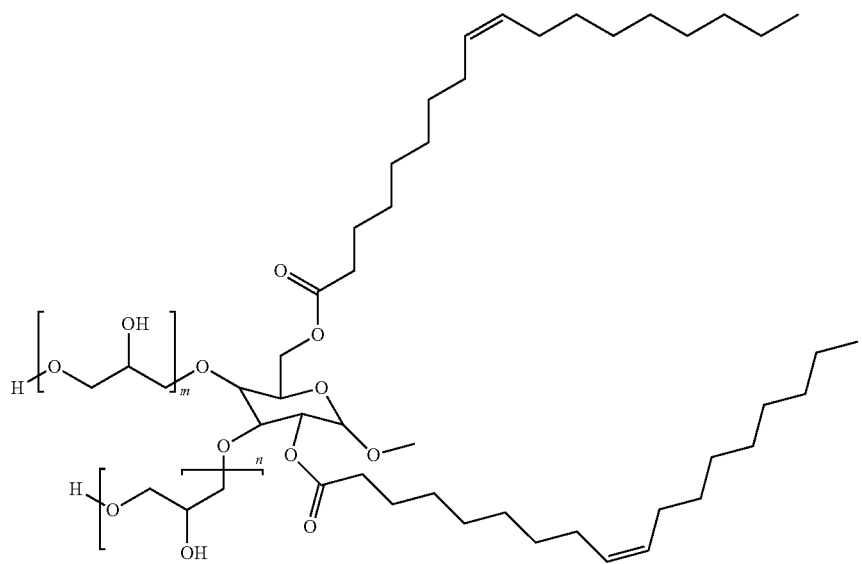

wherein m+n is from greater than 3 to about 11.

20. The composition of claim 19 wherein said composition comprises greater than 50 mol % of said polyglyceryl methyl glucose dioleate compounds.

21. The composition of claim 18 wherein at least one of said one or more compounds is a polyglyceryl sorbitan dioleate compound of the formula:

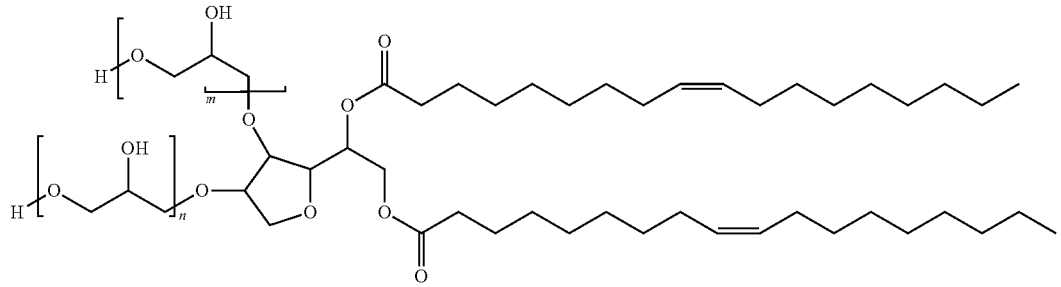

wherein m+n is from greater than 3 to about 11.

22. The composition of claim 19 wherein said composition comprises greater than 50 mol % of said polyglyceryl sorbitan dioleate compounds.

23. The composition of claim 7 wherein at least one of said one or more compounds is a polyglyceryl methyl glucose dioleate compound of the formula:

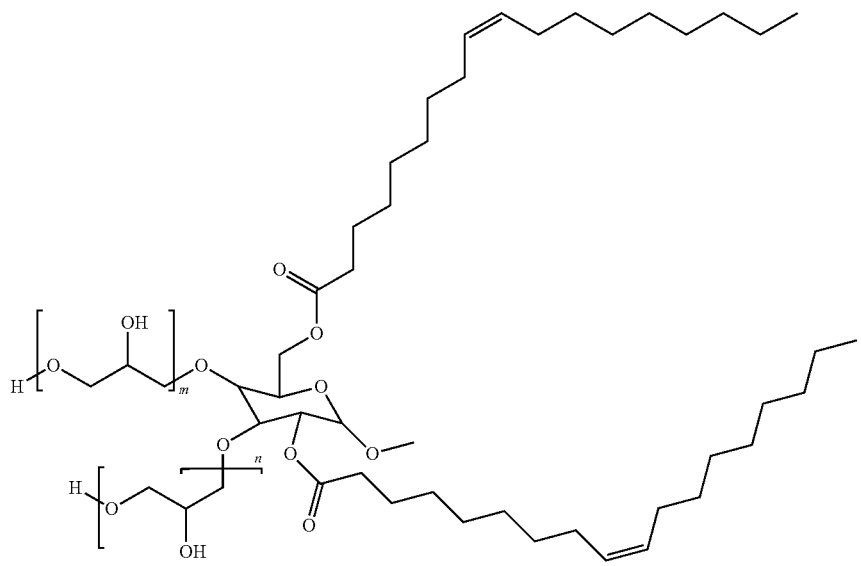

wherein m+n is from about 4 to about 15.

24. The composition of claim 7 wherein at least one of said one or more compounds is a polyglyceryl sorbitan dioleate compound of the formula:

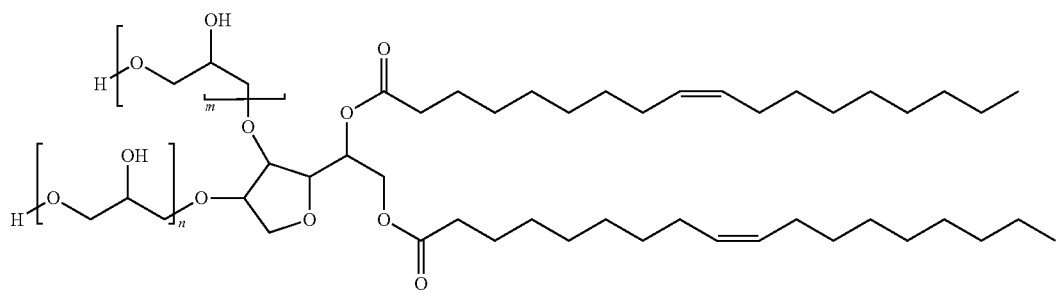

wherein m+n is from about 4 to about 15.

25. The composition of claim 18 wherein at least one of said one or more compounds is a polyglyceryl methyl glucose dioleate compound of the formula:
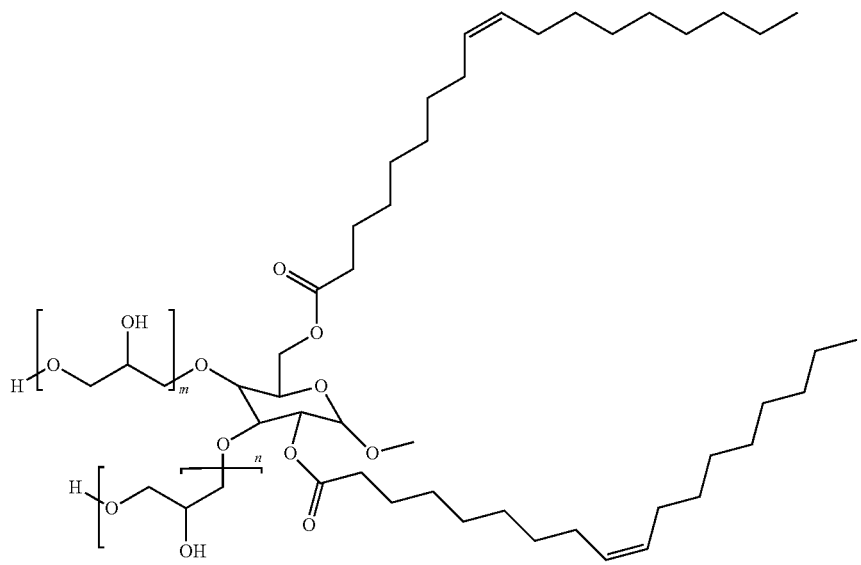
wherein m+n is from about 4 to about 15.
26. The composition of claim 18 wherein at least one of said one or more compounds is a polyglyceryl sorbitan dioleate compound of the formula:
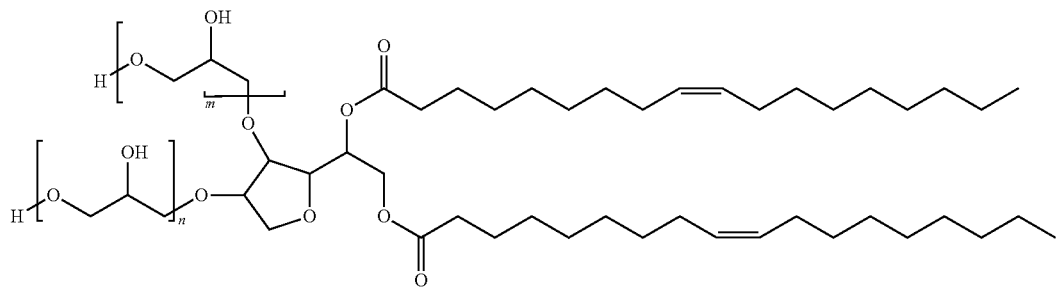
wherein m+n is from about 4 to about 15.
* * * * *